(12) United States Patent
Lee et al.

(10) Patent No.: US 11,613,599 B2
(45) Date of Patent: Mar. 28, 2023

(54) POLYMER COMPOSITION

(71) Applicant: LG Chem, Ltd., Seoul (KR)

(72) Inventors: Eung Chang Lee, Daejeon (KR); Mi Sook Lee, Daejeon (KR); Se Jin Ku, Daejeon (KR); Na Na Kang, Daejeon (KR); Hyung Ju Ryu, Daejeon (KR); Sung Soo Yoon, Daejeon (KR); No Jin Park, Daejeon (KR); Je Gwon Lee, Daejeon (KR); Eun Young Choi, Daejeon (KR); Yoon Hyung Hur, Daejeon (KR)

(73) Assignee: LG Chem, Ltd.

( * ) Notice: Subject to any disclaimer, the term of this patent is extended or adjusted under 35 U.S.C. 154(b) by 274 days.

(21) Appl. No.: 16/757,564

(22) PCT Filed: Nov. 7, 2018

(86) PCT No.: PCT/KR2018/013433
§ 371 (c)(1),
(2) Date: Apr. 20, 2020

(87) PCT Pub. No.: WO2019/093748
PCT Pub. Date: May 16, 2019

(65) Prior Publication Data
US 2020/0347005 A1    Nov. 5, 2020

(30) Foreign Application Priority Data
Nov. 7, 2017  (KR) .................. 10-2017-0147013

(51) Int. Cl.
*C08F 293/00*   (2006.01)
*C08F 214/18*   (2006.01)
*C08L 53/00*    (2006.01)
*B32B 27/00*    (2006.01)
*C07C 65/28*    (2006.01)
*C08F 212/14*   (2006.01)

(52) U.S. Cl.
CPC .......... *C08F 293/005* (2013.01); *B32B 27/00* (2013.01); *C07C 65/28* (2013.01); *C08F 212/20* (2020.02); *C08F 214/186* (2013.01); *C08L 53/00* (2013.01); *B32B 2270/00* (2013.01); *C08F 2438/03* (2013.01)

(58) Field of Classification Search
None
See application file for complete search history.

(56) References Cited

U.S. PATENT DOCUMENTS

| 9,458,353 B1* | 10/2016 | Cheng ..................... C08F 12/22 |
| 2016/0186002 A1 | 6/2016 | Hustad et al. |
| 2016/0319158 A1 | 11/2016 | Fleury et al. |
| 2017/0037178 A1* | 2/2017 | Thackeray .............. G03F 7/322 |
| 2017/0219922 A1 | 8/2017 | Ku et al. |
| 2019/0375904 A1* | 12/2019 | Lee .......................... G03F 1/66 |

FOREIGN PATENT DOCUMENTS

| CN | 105733160 A | 7/2016 |
| CN | 106029759 A | 10/2016 |
| CN | 107078026 A | 8/2017 |
| JP | 2008109152 A | 5/2008 |
| JP | 2013187408 A | 9/2013 |
| JP | 2016128565 A | 7/2016 |
| KR | 20160038704 A | 4/2016 |
| KR | 20160038710 A | 4/2016 |
| KR | 20160098378 A | 8/2016 |
| WO | WO-2016053014 A1 * | 4/2016 ............. B05D 1/005 |

OTHER PUBLICATIONS

Chinese Search Report for Application No. 201880070890.X dated Jul. 2, 2021, 2 Pages.
International Search Report for Application No. PCT/KR2018/013433 dated Feb. 11, 2019, 7 pages.
Kim, "Principle of Block-copolymer (BCP) and Its Application," News & Information for Chemical Engineers, Dec. 2010, pp. 703-707, vol. 28, No. 6.

* cited by examiner

*Primary Examiner* — Nicole M. Buie-Hatcher
(74) *Attorney, Agent, or Firm* — Lerner, David, Littenberg, Krumholz & Mentlik, LLP

(57) ABSTRACT

Methods for forming a laminate are provided. The method provides a highly aligned block copolymer without orientation defects, coordination number defects distance defects and the like on a substrate, thereby providing a laminate which can be effectively applied to the production of various patterned substrates, and a method for producing a patterned substrate using the same.

14 Claims, 4 Drawing Sheets

[Figure 1]
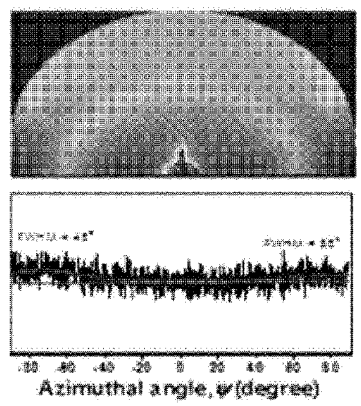
[Figure 2]
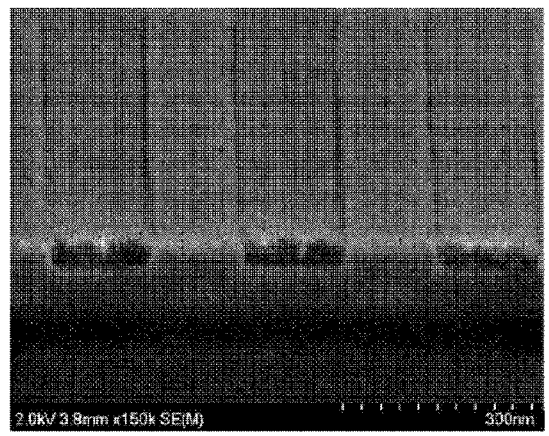
[Figure 3]
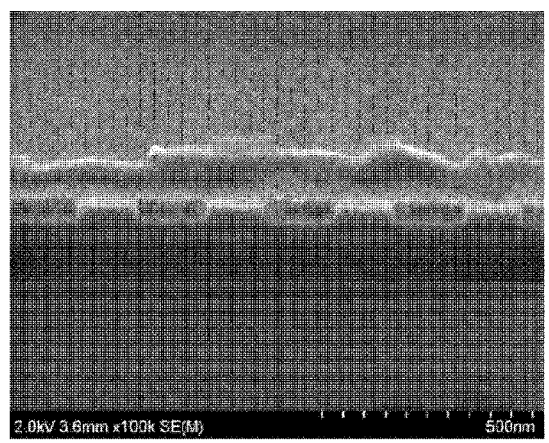

[Figure 4]
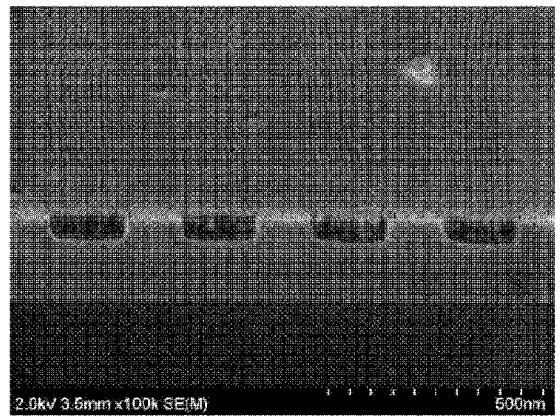
[Figure 5]
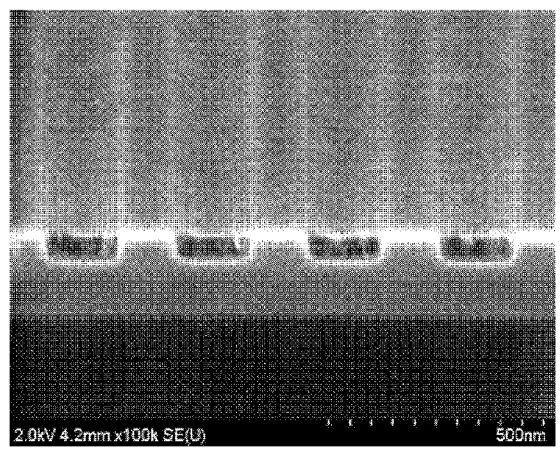
[Figure 6]
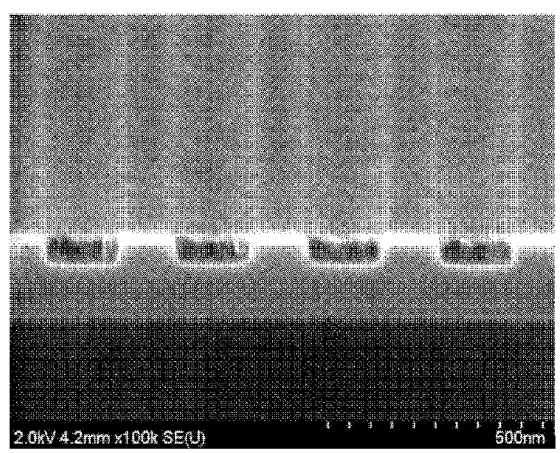

[Figure 7]
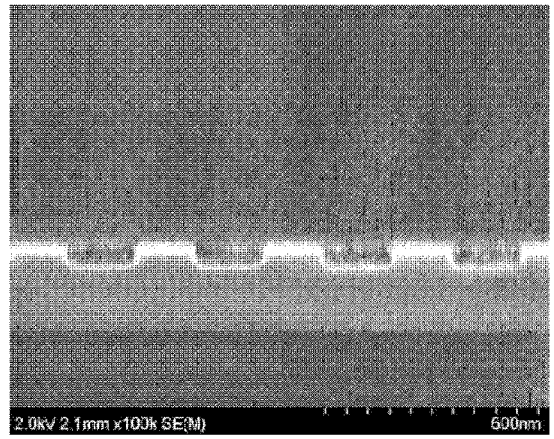
[Figure 8]
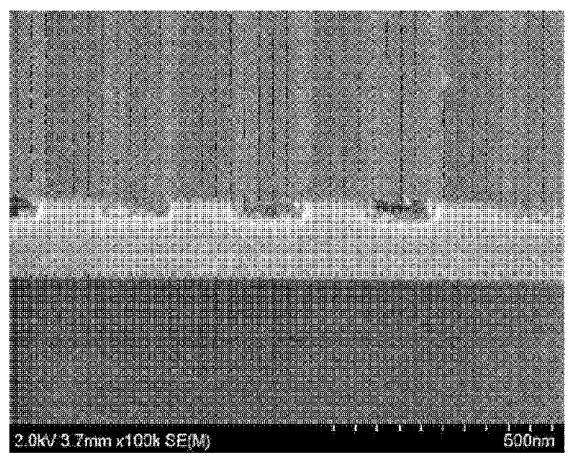
[Figure 9]
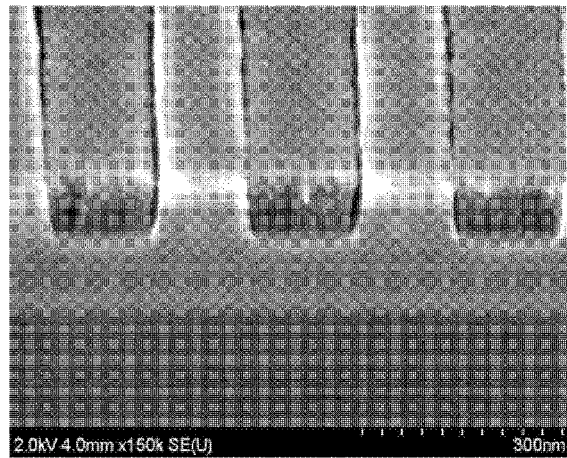

[Figure 10]
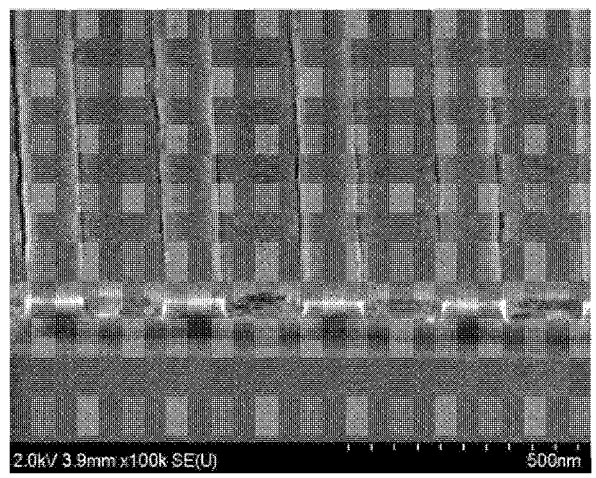

POLYMER COMPOSITION

CROSS-REFERENCE TO RELATED APPLICATIONS

The present application is a national phase entry under 35 U.S.C. § 371 of International Application No PCT/KR2018/013433 filed Nov. 7, 2018 which claims priority from Korean Patent Application No. 10-2017-0147013 filed on Nov. 7, 2017, the disclosures of which are incorporated herein by reference in their entirety.

TECHNICAL FIELD

The present application relates to a polymer composition.

BACKGROUND ART

A block copolymer has a molecular structure in which polymer blocks having different chemical structures are linked via covalent bonds. The block copolymer can form a periodically arranged structure such as a sphere, a cylinder or a lamella by phase separation. The shape and size of the domain of the structure formed by a directed self-assembly phenomenon of the block copolymer can be controlled by, for example, the kind of the monomer forming each block or the relative ratio between the blocks, and the like.

Due to such a characteristic, the block copolymer is being considered for applications to nanowire fabrication, fabrication of next-generation nano elements such as quantum dots or metal dots or a lithography method capable of forming a high-density pattern on a predetermined substrate, and the like.

The technique of orienting the self-assembled structure of the block copolymer horizontally or vertically on various substrates occupies a very large proportion in the application of the block copolymer. Typically, the orientation of the nanostructure formed by self-assembly of the block copolymer is determined depending on which block of the block copolymer is exposed to the surface or air. In general, many substrates are polar and air is non-polar. Therefore, a block having a larger polarity among the blocks of the block copolymer is wetted to the substrate and a block having a smaller polarity is wetted to the interface with the air, so that in general, the nanostructures formed by the self-assembly of the block copolymer are oriented horizontally with respect to the substrate.

However, a technique is preferred, in which different blocks constituting the block copolymer are simultaneously wetted on the substrate side so that the above-described nanostructures are oriented perpendicularly with respect to the substrate. Accordingly, in order for the above-described nanostructures to be vertically oriented with respect to the substrate, various methods have been proposed, and among them, the most typical method is a method of forming a neutral surface for different blocks constituting the block copolymer on a substrate.

DISCLOSURE

Technical Problem

It is one object of the present application to provide a polymer composition in which self-assembled structures of a block copolymer can be oriented vertically with respect to a substrate without application of a neutral layer.

Technical Solution

In the present application, the term "monovalent or divalent hydrocarbon group" may mean a monovalent or divalent residue derived from a compound composed of carbon and hydrogen or a derivative thereof, unless otherwise specified. Here, the compound composed of carbon and hydrogen can be exemplified by alkane, alkene, alkyne, or aromatic hydrocarbon.

In the present application, the term "alkyl group" may mean an alkyl group having 1 to 20 carbon atoms, 1 to 16 carbon atoms, 1 to 12 carbon atoms, 1 to 8 carbon atoms or 1 to 4 carbon atoms, unless otherwise specified. The alkyl group may be a linear, branched or cyclic alkyl group, which may be optionally substituted by one or more substituents.

In the present application, the term "alkoxy group" may mean an alkoxy group having 1 to 20 carbon atoms, 1 to 16 carbon atoms, 1 to 12 carbon atoms, 1 to 8 carbon atoms, 1 to 4 carbon atoms or 1 to 2 carbon atoms, unless otherwise specified. The alkoxy group may be a linear, branched or cyclic alkoxy group, which may be optionally substituted by one or more substituents.

In the present application, the term "alkenyl group" or "alkynyl group" means an alkenyl group or alkynyl group having 2 to 20 carbon atoms, 2 to 16 carbon atoms, 2 to 12 carbon atoms, 2 to 8 carbon atoms or 2 to 4 carbon atoms, unless otherwise specified. The alkenyl or alkynyl group may be linear, branched or cyclic, which may be optionally substituted by one or more substituents.

In the present application, the term "alkylene group" may mean an alkylene group having 1 to 20 carbon atoms, 1 to 16 carbon atoms, 1 to 12 carbon atoms, 1 to 8 carbon atoms or 1 to 4 carbon atoms, unless otherwise specified. The alkylene group may be a linear, branched or cyclic alkylene group, which may be optionally substituted by one or more substituents.

In the present application, the term "alkenylene group" or "alkynylene group" may mean an alkenylene group or alkynylene group having 2 to 20 carbon atoms, 2 to 16 carbon atoms, 2 to 12 carbon atoms, 2 to 8 carbon atoms or 2 to 4 carbon atoms. The alkenylene group or alkynylene group may be linear, branched or cyclic, which may be optionally substituted by one or more substituents.

In the present application, the term "aryl group" or "arylene group" may mean, unless otherwise specified, a monovalent residue or divalent residue derived from a compound comprising one benzene structure, or a structure in which two or more benzene rings are linked while sharing one or two carbon atoms, or linked by any linker, or a derivative thereof The aryl group or arylene group may be, for example, an aryl group having 6 to 30 carbon atoms, 6 to 25 carbon atoms, 6 to 21 carbon atoms, 6 to 18 carbon atoms, 6 to 13 carbon atoms or unless otherwise specified.

In the present application, the term "aromatic structure" may mean the aryl group or arylene group.

In the present application, the term "alicyclic ring structure" means a cyclic hydrocarbon structure other than an aromatic ring structure, unless otherwise specified. The alicyclic ring structure may be, for example, an alicyclic ring structure having 3 to 30 carbon atoms, 3 to 25 carbon atoms, 3 to 21 carbon atoms, 3 to 18 carbon atoms or 3 to 13 carbon atoms, unless otherwise specified.

In the present application, the term "single bond" may mean a case where no separate atom is present at the relevant site. For example, in the structure represented by A-B-C, when B is a single bond, no separate atom exists at the site represented by B, and A and C are directly connected, so that it may mean to form a structure represented by A-C.

In the present application, the substituent, with which the alkyl group, alkenyl group, alkynyl group, alkylene group, alkenylene group, alkynylene group, alkoxy group, aryl group, arylene group, linear chain or aromatic structure, and the like may be optionally substituted, may be exemplified by a hydroxy group, a halogen atom, a carboxyl group, a glycidyl group, an acryloyl group, a methacryloyl group, an acryloyloxy group, a methacryloyloxy group, a thiol group, an alkyl group, an alkenyl group, an alkynyl group, an alkylene group, an alkenylene group, an alkynylene group, an alkoxy group or an aryl group, and the like, but is not limited thereto.

In the present application, the fact that a certain polymer (a polymer such as a block copolymer or a random copolymer) contains a certain unit of a compound may mean that the compound undergoes a polymerization reaction to form a skeleton in the polymer.

The present application relates to a polymer composition. The polymer composition of the present application may also be applied to a method for producing a patterned substrate to be described below. Specifically, the method may be performed by a lithography method in which a directed self-assembly material is applied as a template. Here, the directed self-assembly material may also be a block copolymer included in the polymer composition. That is, the polymer composition of the present application may comprise a block copolymer.

In one example, the block copolymer may comprise a polymer segment A, and a polymer segment B different from the polymer segment A.

In the present application, the fact that two kinds of polymer segments are identical is a case where 50% or more, 55% or more, 60% or more, 65% or more, 70% or more, 75% or more, 80% or more, 85% or more or 90% or more of monomer units contained in any two kinds of polymer segments are common and a weight ratio deviation of the common monomer units in each polymer segment is within 30%, within 25%, within 20%, within 15%, within 10% or within 5%. Therefore, if both polymer segments do not satisfy the above condition, they are polymer segments that are different from each other. Here, it may be proper that the ratio of the common monomer units is satisfied for both polymer segments. For example, if any polymer segment 1 has monomer units of A, B, C, D and F and the other polymer segment 2 has monomer units of D, F, G and H, then the common monomer units in polymer segments 1 and 2 are D and F, where in the position of polymer segment 1 the common ratio is 40% (=100×2/5) because two kinds of the total five kinds are common, but in the position of polymer segment 2 the ratio is 50% (=100×2/5). Thus, in this case, both polymer segments may be regarded as not identical because the common ratio is not less than 50% only in polymer segment 2. On the other hand, the weight ratio deviation of the common monomers is a percentage of a numerical value in which a large weight ratio minus a small weight ratio is divided by the small weight ratio. For example, in the above case, if the weight ratio of the D monomer units in the segment 1 is about 40% based on 100% of the total weight ratio of the whole monomer units in the segment 1 and the weight ratio of the D monomer units in the segment 2 is about 30% based on 100% of the total weight ratio of the whole monomer units in the segment 2, the weight ratio deviation may be about 33% (=100×(40−30)/30) or so. If the common monomer units are two or more kinds in two segments, in order to be the same segment, it can be considered as the common monomers when the weight ratio deviation within 30% is satisfied for all the common monomers or for the monomer unit as the main component. Each polymer segment that is recognized as the same by the above criteria may be a different type of polymer (e.g., any one segment is in the form of a block copolymer and the other segment is in the form of a random copolymer), but it may be, suitably, the same type of polymer.

In one example, each of the polymer segments of the block copolymer may be formed of only one type of monomer, or may be formed of two or more types of monomers. Also, the block copolymer may be a diblock copolymer containing only one polymer segment A and one polymer segment B.

In another example, the block copolymer may also be a block copolymer having three blocks or more which comprises each of the polymer segments A and B by one and further comprises either or both of the polymer segments A and B, or further comprises other polymer segments rather than the polymer segments A and B.

Since block copolymers contain two or more different polymer segments connected by covalent bonds, phase separation between the polymer segments can occur. Accordingly, the block copolymer can form a so-called self-assembled structure.

The inventors of the present invention have confirmed that when any of the block copolymers satisfies one or two or more of conditions to be described below, it can be more effectively applied in the laminate. Accordingly, the block copolymer of the present application may satisfy at least one of the conditions to be described below. The conditions to be described below are in parallel, and any one condition does not override the other conditions. Specifically, the block copolymer contained in the polymer composition of the present application may satisfy any one of the conditions to be described below, or may satisfy two or more conditions.

In one example, if the block copolymer meets any one of the conditions to be described below, the self-assembled structure formed by the block copolymer can be vertically oriented with respect to the substrate to be described later.

In the present application, the fact that the self-assembled structure formed by the block copolymer is vertically aligned with respect to the substrate may mean that any one of the polymer segments constituting the block copolymer and the polymer segment different from the polymer segment are all oriented in a state of being wetted on the substrate, and specifically, may mean a case where the interface formed by the domains formed by any one of the polymer segments constituting the block copolymer and the domains formed by the different polymer segment is perpendicular to the surface of the substrate.

In the present application, the term vertical is an expression in consideration of an error, which may be a meaning including, for example, errors within ±10 degrees, ±8 degrees, ±6 degrees, ±4 degrees or ±2 degrees.

In one example, the absolute value of the difference between the surface energy of the polymer segment A and the surface energy of the polymer segment B in the block copolymer may be 10 mN/m or less. In another example, the value may be 9 mN/m or less, 8 mN/m or less, 7.5 mN/m or less, and may be 1.5 mN/m or more, 2 mN/m or more, or 2.5 mN/m or more. The block copolymer comprising the polymer segments A and B satisfying the above condition can induce an effective fine phase separation when forming a self-assembled structure.

In the present application, the surface energy can be measured using a drop shape analyzer (DSA100, KRUSS). Specifically, the surface energy can be measured in the following order:

(1) A coating solution is prepared by diluting a sample (block copolymer or homopolymer) to be measured in fluorobenzene to a solid concentration of about 2 wt %.

(2) The coating solution is coated on a substrate to a thickness of about 50 nm and a coating area of 4 cm² (width: 2 cm, height: 2 cm), and dried at room temperature for about 1 hour.

(3) After drying, thermal annealing is performed at a temperature of 160° C. for about 1 hour.

(4-1) Deionized water, whose surface tension is known, is dropped on the membrane subjected to the thermal annealing according to Step (3) and the contact angle of deionized water is measured using the drop shape analyzer, and then, the above process is repeated five times to obtain an arithmetic mean value of the obtained five contact angle values.

(4-2) Diiodomethane, whose surface tension is known, is dropped on the membrane subjected to the thermal annealing according to Step (3) and the contact angle of diiodomethane is measured using the drop shape analyzer, and then, the above process is repeated five times to obtain an arithmetic mean value of the obtained five contact angle values.

(5) The contact angle values obtained in Steps (4-1) and (4-2) above, respectively, are applied to the Owens-Wendt-Rabel-Kaelble method, wherein the surface energy is obtained by substituting, as the required numerical value regarding the surface tension for each solvent, the known (Strom) value for each solvent.

Here, the surface energy of any one of the polymer segments constituting the block copolymer may mean the surface energy measured by applying the above-described method to the homopolymer produced by only the monomer forming the polymer segment.

When the block copolymer comprises side chains to be described below, the polymer segment comprising the side chains may have a higher surface energy than the polymer segment without any side chain. For example, if the polymer segment A of the block copolymer comprises the side chain, the polymer segment A may have a higher surface energy than the polymer segment B. In this case, the surface energy of the polymer segment A may be in a range of about 20 mN/m to 50 mN/m. The surface energy of the polymer segment A may be 22 mN/m or more, 24 mN/m or more, 26 mN/m or more, or 28 mN/m or more. The surface energy of the polymer segment A may be 48 mN/m or less, 46 mN/m or less, 44 mN/m or less, or 42 mN/m or less. The block copolymer comprising such a polymer segment A can exhibit excellent self-assembly properties.

In one example, the polymer segment A may exhibit a melting transition peak or an isotropic transition peak in a range of −80° C. to 200° C. in a DSC analysis (Condition 1).

In another example, the polymer segment A may exhibit a peak having a half-value width in a range of 0.2 to 0.9 $nm^{-1}$ within a scattering vector (q) range of 0.5 $nm^{-1}$ to 10 $nm^{-1}$ upon an XRD analysis (Condition 2).

In another example, the polymer segment A may comprise a side chain and the number (n) of chain-forming atoms in the side chain and the scattering vector (q) obtained by the XRD analysis of the polymer segment A may satisfy Equation 1 below (Condition 3).

$$3 \text{ nm}^{-1} \leq nq/(2\times\pi) \leq 5 \text{ nm}^{-1} \quad \text{[Equation 1]}$$

In Equation 1, n is a number of chain-forming atoms of the side chain, and q is the smallest scattering vector (q) in which the peak is observed in the X-ray diffraction analysis for the polymer segment containing the side chain, or the scattering vector (q) in which the peak of the largest peak area is observed.

In one example, the block copolymer comprises a polymer segment A and a polymer segment B different from the polymer segment A, wherein the absolute value of the difference in density between the polymer segment A and the polymer segment B may be 0.25 $g/cm^3$ or more (Condition 4).

In the respective block copolymers, the polymer segment A may be a polymer segment comprising a side chain as described below.

Hereinafter, each of the conditions will be described in detail.

In the present application, physical properties, such as density, that can be changed by temperature are values measured at room temperature, unless otherwise specified. Also, the term room temperature may mean a natural temperature without warming or cooling, which may mean, for example, a temperature at any one point of about 10° C. to 30° C., or a temperature of about 25° C. or about 23° C.

A. Condition 1

Any one polymer segment of the block copolymer of the present application may exhibit a melting transition peak or isotropic transition peak in a range of −80° C. to 200° C. in a DSC (differential scanning calorimetry) analysis. Any one polymer segment of the block copolymer may also exhibit only any peak of the melting transition peak and the isotropic transition peak, or may exhibit both of the two peaks. Such a block copolymer may be a block copolymer exhibiting a crystal phase and/or a liquid crystal phase suitable for self-assembly as a whole or may be a copolymer comprising a polymer segment exhibiting such a crystal phase and/or a liquid crystal phase. Any one of the polymer segments satisfying Condition 1 above may be a polymer segment A as described above.

Any one of the polymer segments of the block copolymer showing the DSC behavior as described above can further satisfy the following conditions.

Specifically, when the isotropic transition peak and the melting transition peak appear simultaneously, the difference (Ti−Tm) between the temperature (Ti) at which the isotropic transition peak appears and the temperature (Tm) at which the melting transition peak appears may be in a range of 5° C. to 70° C. In another example, the difference (Ti−Tm) may be 10° C. or more, 15° C. or more, 20° C. or more, 25° C. or more, 30° C. or more, 35° C. or more, 40° C. or more, 45° C. or more, 50° C. or more, 55° C. or more, or 60° C. or more. The block copolymer comprising the polymer segments having a difference (Ti−Tm) between the temperature (Ti) of the isotropic transition peak and the temperature (Tm) of the melting transition peak in the above range can maintain excellent phase separation or self-assembly characteristics.

In another example, when the isotropic transition peak and the melting transition peak appear simultaneously, the ratio (M/I) of the area (I) of the isotropic transition peak and the area (M) of the melting transition peak may be in a range of 0.1 to 500. In the DSC analysis, the block copolymer comprising the polymer segments having a ratio (M/I) of the area (I) of the isotropic transition peak and the area (M) of the melting transition peak in the above range can maintain excellent phase separation or self-assembly characteristics. In another example, the ratio (M/I) may be 0.5 or more, 1 or more, 1.5 or more, 2 or more, 2.5 or more, or 3 or more, and may be 450 or less, 400 or less, 350 or less, 300 or less, 250 or less, 200 or less, 150 or less, 100 or less, 90 or less, or 85 or less.

A method of performing the DSC analysis is known, and in the present application, the above analysis can be performed by such a known method.

The temperature (Tm) range at which the melting transition peak appears may be a range of −10° C. to 55° C. In another example, the temperature (Tm) may be 50° C. or less, 45° C. or less, 40° C. or less, 35° C. or less, 30° C. or less, 25° C. or less, 20° C. or less, 15° C. or less, 10° C. or less, 5° C. or less, or 0° C. or less.

The block copolymer may comprise a polymer segment having a side chain, as described below. In this case, the block copolymer may satisfy Equation 2 below:

$$10° \text{ C.} \leq Tm - 12.25° \text{ C.} \times n + 149.5° \text{ C.} \leq 10° \text{ C.} \quad \text{[Equation 2]}$$

In Equation 2, Tm is a temperature at which the polymer segment having the side chain exhibits a melting transition peak, and n is a number of chain-forming atoms of the side chain The block copolymer satisfying Equation above can exhibit excellent phase separation or self-assembly properties.

In another example, Tm−12.25° C.×n+149.5° C. in Equation 2 may be −8° C. to 8° C., −6° C. to 6° C., or −5° C. to 5° C. or so.

B. Condition 2

The block copolymer of the present application may comprise a polymer segment showing at least one peak in a predetermined range of the scattering vector (q) upon the XRD analysis (X-ray diffraction analysis). The polymer segment satisfying Condition 2 may be the polymer segment A.

For example, any one polymer segment of the block copolymer may exhibit at least one peak in a scattering vector (q) range of 0.5 nm$^{-1}$ to 10 nm$^{-1}$ in the X-ray diffraction analysis. In another example, the scattering vector (q) at which the peak appears may be 0.7 nm$^{-1}$ or more, 0.9 nm$^{-1}$ or more, 1.1 nm$^{-1}$ or more, 1.3 nm$^{-1}$ or more, or 1.5 nm$^{-1}$ or more, and may be 9 nm$^{-1}$ or less, 8 nm$^{-1}$ or less, 7 nm$^{-1}$ or less, 6 nm$^{-1}$ or less, 5 nm$^{-1}$ or less, 4 nm$^{-1}$ or less, 3.5 nm$^{-1}$ or less, or 3 nm$^{-1}$ or less. The half-value width (full width at half maximum, FWHM) of the peak identified in the above scattering vector (q) range may be in the range of 0.2 to 0.9 nm$^{-1}$. In another example, the half-value width may be 0.25 nm$^{-1}$ or more, 0.3 nm$^{-1}$ or more, or 0.4 nm$^{-1}$ or more. In another example, the half-value width may be 0.85 nm$^{-1}$ or less, 0.8 nm$^{-1}$ or less, or 0.75 nm$^{-1}$ or less.

In Condition 2, the term half-value width may mean a width of the peak (the difference in the scattering vector (q)) at a position showing the ½ intensity of the maximum peak intensity.

The scattering vector (q) and the half-value width in the XRD analysis are values obtained by a numerical analytical method in which the results obtained by the XRD analysis to be described below are applied by a least-square method. In the method, the profile of the XRD patterns is subjected to Gaussian fitting in a state where a portion showing the smallest intensity in the XRD diffraction patterns is taken as a baseline and the intensity in the above is set to zero, and then the scattering vector and the half-value width can be obtained from the fitted results. The R square at the time of Gaussian fitting is at least 0.9 or more, 0.92 or more, 0.94 or more, or 0.96 or more. A method capable of obtaining the information as above from the XRD analysis is known, and for example, a numerical analysis program such as Origin can be applied.

The polymer segment showing the peak of the half-value width in the above scattering vector (q) range may comprise a crystalline site suitable for self-assembly. The block copolymer comprising the polymer segment identified in the above-described scattering vector (q) range may exhibit excellent self-assembly properties.

The XRD analysis can be performed by transmitting X-rays to a sample and then measuring the scattering intensity according to the scattering vector. The XRD analysis can be performed using a polymer prepared by polymerizing only a monomer constituting any one polymer segment of the block copolymer, for example, the polymer segment A. The XRD analysis can be performed on such a polymer without any special pretreatment, and for example, can be performed by drying the polymer under appropriate conditions and then passing it through X-rays. As the X-ray, an X-ray having a vertical size of 0.023 mm and a horizontal size of 0.3 mm can be applied. The scattering vector and the half-value width can be obtained by obtaining as an image 2D diffraction patterns that are scattered in the sample and exited using a measuring instrument (for example, 2D marCCD), and fitting the obtained diffraction pattern with the above-described manner.

C. Condition 3

The block copolymer of the present application may comprise, as the polymer segment A, a polymer segment having a side chain to be described below. At this time, the number (n) of chain-forming atoms of the side chain and the scattering vector (q) obtained by the X-ray diffraction analysis performed in the same manner as in Condition 2 above can satisfy Equation 1 below.

$$3 \text{ nm}^{-1} \leq nq/(2 \times \pi) \leq 5 \text{ nm}^{-1} \quad \text{[Equation 1]}$$

In Equation 1, n is a number of the chain-forming atoms, and q is the smallest scattering vector (q) in which the peak is observed in the X-ray diffraction analysis for the polymer segment containing the side chain, or the scattering vector (q) in which the peak of the largest peak area is observed. Also, in Equation 1, π means the circular constant.

The scattering vector or the like introduced into Equation 1 is a value obtained by the same manner mentioned in the above-described X-ray diffraction analysis method.

The scattering vector (q) introduced in Equation 1 may be, for example, a scattering vector (q) in a range of 0.5 nm$^{-1}$ to 10 nm$^{-1}$, and may be 0.7 nm$^{-1}$ or more, 0.9 nm$^{-1}$ or more, 1.1 nm$^{-1}$ or more, 1.3 nm$^{-1}$ or more, or 1.5 nm$^{-1}$ or more. In another example, the scattering vector (q) introduced into Equation 1 above may be 9 nm$^{-1}$ or less, 8 nm$^{-1}$ or less, 7 nm$^{-1}$ or less, 6 nm$^{-1}$ or less, 5 nm$^{-1}$ or less, 4 nm$^{-1}$ or less, 3.5 nm$^{-1}$ or less, or 3 nm$^{-1}$ or less.

When a polymer composed of only the polymer segment comprising the side chain of the block copolymer has formed a membrane, Equation 1 may mean a relationship of the distance (D) between the polymer main chains containing the side chains and the number of chain-forming atoms in the side chain. In addition, when the number of chain-forming atoms of the side chain in the polymer having the side chain satisfies Equation 1 above, the crystallinity represented by the side chain is increased, whereby the phase separation property or the vertical orientation can be significantly improved. In another example, the nq/(2×π) according to Equation 1 above may also be 4.5 nm$^{-1}$ or less. Here, the distance (D, unit: nm) between the polymer main chains in which the side chains are contained can be calculated by the equation $D=2\times\pi/q$, where D is the distance (D, unit: nm), and $\pi$ and q are as defined in Equation 1.

D. Condition 4

The block copolymer of the present application may comprise a polymer segment A, and a polymer segment B different from the polymer segment A, and the absolute value of the difference in density between the polymer segment A and the polymer segment B in the block copolymer may be 0.25 g/cm$^3$ or more, 0.3 g/cm$^3$ or more, 0.35 g/cm$^3$ or more, 0.4 g/cm$^3$ or more, or 0.45 g/cm$^3$ or more. The absolute value of the difference in density may be 0.9 g/cm$^3$ or less, 0.8 g/cm$^3$ or less, 0.7 g/cm$^3$ or less, or 0.65 g/cm$^3$ or less.

The density of each polymer segment in the block copolymer can be measured using a known buoyancy method. As a method of measuring the density of each polymer segment constituting the block copolymer, for example, a method of analyzing the mass of the block copolymer in a solvent in which mass and density in air are known, such as ethanol, can be used.

In one example, when any one of the polymer segments of the block copolymer comprises a side chain to be described below, the polymer segment comprising the side chain may have a lower density than the polymer segment without any side chain. For example, if the polymer segment A of the block copolymer comprises a side chain and the polymer segment B does not comprise a side chain, the density of the polymer segment A may be lower than the density of the polymer segment B. In this case, the density of the polymer segment A may be in a range of about 0.9 g/cm$^3$ to about 1.5 g/cm$^3$. In another example, the density of the polymer segment A may be 0.95 g/cm$^3$ or more, and may be 1.4 g/cm$^3$ or less, 1.3 g/cm$^3$ or less, 1.2 g/cm$^3$ or less, 1.1 g/cm$^3$ or less, or 1.05 g/cm$^3$ or less.

As described above, the block copolymer may satisfy any of the above conditions, or may satisfy two or more conditions selected from the above conditions.

In one example, the block copolymer comprises a polymer segment A satisfying at least one of Conditions 1 to 3 above; and a polymer segment B satisfying Condition 4 above.

Although not limited by theory, the polymer segment A satisfying any one of Conditions 1 to 3 can exhibit crystallinity or liquid crystallinity. When the block copolymer comprising such a polymer segment A forms a self-assembled structure, it can be packed with regularity. Furthermore, when the polymer segment B different from the polymer segment A satisfies Condition 4, the domains formed by the respective polymer segments A and B may be substantially neutralized. Accordingly, the self-assembled structure formed by the block copolymer can be vertically oriented within the structure of the laminate to be described below.

According to one example, in the block copolymer, the polymer segment A may have a volume fraction in s range of 0.3 to 0.8, and the sum of the volume fractions of the polymer segment A and the polymer segment B may be 1. In another example, the volume fraction of the polymer segment A may be 0.30 or more, 0.32 or more, 0.34 or more, 0.36 or more, 0.38 or more, 0.40 or more, and may be 0.7 or less, 0.67 or less, 0.64 or less, 0.62 or less, or 0.60 or less. The block copolymer comprising the respective segments as described above at the above volume fractions can exhibit excellent self-assembly properties in a laminate to be described below.

In the present application, a volume fraction of a component constituting a certain polymer (for example, block copolymer or random copolymer, etc.) can be obtained based on the density of the component and the molecular weight by GPC (gel permeation chromatography) or NMR (nuclear magnetic resonance), the ratio of the number of hydrogen atoms having 1 mole of the repeating unit constituted of the component, and the molecular weight of the component.

In another example, the block copolymer may have a number average molecular weight (Mn) in a range of, for example, 5,000 to 100,000. In this specification, the term number average molecular weight is a converted value relative to standard polystyrene measured using GPC (gel permeation chromatograph), and in the present application, the term molecular weight means a number average molecular weight, unless otherwise specified. In addition, the unit of molecular weight is g/mol, unless otherwise specified. In another example, the molecular weight (Mn) of the block copolymer may be in a range of 5000 or more, 7000 or more, 9000 or more, 11000 or more, 12000 or more, 13000 or more, or 14000 or more. In yet another example, the molecular weight (Mn) may be 100000 or less, 90000 or less, 80000 or less, 70000 or less, 60,000 or less, 50,000 or less, 40,000 or less, 30,000 or less, or 25,000 or less or so.

In one example, the block copolymer may have polydispersity (Mw/Mn) in a range of 1.01 to 1.60. In an example, the value may be about 1.01 or more, about 1.02 or more, about 1.03 or more, about 1.04 or more, about 1.05 or more, about 1.06 or more, about 1.07 or more, about 1.08 or more, and may be about 1.60 or less, about 1.58 or less, about 1.56 or less, 1.54 or less, 1.52 or less, 1.50 or less, 1.48 or less, 1.46 or less, 1.44 or less, 1.42 or less, or 1.40 or less, but is not limited thereto.

In the above, the number average molecular weight or the polydispersity, and the like of the block copolymer may be adjusted in consideration of the desired self-assembled structure.

The above-mentioned conditions can be achieved, for example, by controlling the structure of the block copolymer. For example, the polymer segment A of the block copolymer satisfying one or more of the above-mentioned conditions may comprise the side chain to be described below. Specifically, the polymer segment A may comprise a ring structure, where the above-mentioned side chain may be substituted on the ring structure. In addition, the side chain may also be directly substituted on the ring structure or may be substituted via a suitable linker. The ring structure may be an aromatic structure or an alicyclic ring structure as described above. No halogen atom may also be present in the ring structure contained in the polymer segment A.

In another example, the polymer segment B contained in the block copolymer together with the polymer segment A may comprise 3 or more halogen atoms. That is, a halogen atom may be present in the ring structure included in the polymer segment B. At this time, the polymer segment B may comprise a ring structure, where the halogen atoms may be substituted on the ring structure. The ring structure may be an alicyclic ring structure or an aromatic structure as described above.

Here, the aromatic structure or the alicyclic ring structure may be a structure contained in the main chain of the polymer segment, or may be a structure linked to the polymer segment main chain in a side chain form.

As will be described below, the side chain contained in the polymer segment A may be a side chain having 8 or more chain-forming atoms. Such a polymer segment A may be a polymer segment satisfying at least one of Conditions 1 to 3 as described above.

Here, the term side chain may mean a chain connected to the main chain of the polymer. In addition, the term chain-forming atom means an atom forming the side chain, specifically, the straight chain structure of the chain. The side chain may be linear or branched, and the number of chain-forming atoms is calculated by only the number of atoms forming the longest straight chain, where other atoms bonded to the chain-forming atoms (for example, when the chain-forming atom is a carbon atom, hydrogen atoms bonding to the carbon atom, etc.) are not included in the calculation of the number of the chain-forming atoms. For example, when the above chain is a branched chain, the number of chain-forming atoms can be calculated as the number of chain-forming atoms forming the longest chain moiety. For example, when the side chain is an n-pentyl group, all of the chain-forming atoms are carbon atoms and the number thereof is 5, and even when the side chain is a 2-methylpentyl group, all of the chain-forming atoms are carbon atoms and the number thereof is 5. The chain-forming atom may be exemplified by carbon, oxygen, sulfur or nitrogen, and the like, and the appropriate chain-forming atom may be carbon, oxygen or nitrogen, or may be carbon or oxygen. In another example, the number of chain-forming atoms may be 8 or more, 9 or more, 10 or more, 11 or more, or 12 or more, and may be 30 or less, 25 or less, 20 or less, or 16 or less.

For the control of the above-described conditions, the polymer segment A of the block copolymer may also have a chain with 8 or more chain-forming atoms connected to the side chain. In this specification, the term chain and side chain may refer to the object identical to each other.

As described above, the side chain may be comprising 8 or more, 9 or more, 10 or more, 11 or more, or 12 or more chain-forming atoms, and may be a chain comprising 30 or less, 25 or less, 20 or less, or 16 or less chain-forming atoms. The chain-forming atom may be a carbon, oxygen, nitrogen or sulfur atom and may suitably be carbon or oxygen.

An example of the side chain may include a hydrocarbon chain such as an alkyl group, an alkenyl group or an alkynyl group. In another example, at least one of carbon atoms of the hydrocarbon chain may be substituted with a sulfur atom, an oxygen atom, or a nitrogen atom.

When the side chain is connected to the ring structure, the chain may be directly connected to the ring structure, or may be connected via a linker. The linker may be exemplified by an oxygen atom, a sulfur atom, —NR$_1$—, —S(=O)$_2$—, a carbonyl group, an alkylene group, an alkenylene group, an alkynylene group, —C(=O)—X$_1$— or —X$_1$—C(=O)—. Here, R$_1$ may be hydrogen, an alkyl group, an alkenyl group, an alkynyl group, an alkoxy group or an aryl group. Here, X$_1$ may be a single bond, an oxygen atom, a sulfur atom, —NR$_2$—, an alkylene group, an alkenylene group or an alkynylene group. Here, R$_2$ may be hydrogen, an alkyl group, an alkenyl group, an alkynyl group, an alkoxy group or an aryl group. The suitable linker may be exemplified by an oxygen atom. The side chain may be connected to a ring structure such as an aromatic structure or an alicyclic structure, for example, via an oxygen atom or a nitrogen atom.

When the above-described ring structure is connected to the main chain of the polymer segment in a side chain form, the ring structure may also be directly connected to the main chain or may be connected via a linker. In this case, the linker can be exemplified by an oxygen atom, a sulfur atom, —S(=O)$_2$—, a carbonyl group, an alkylene group, an alkenylene group, an alkynylene group, —C(=O)—X$_1$— or —X$_1$—C(=O)—, where X$_1$ may be a single bond, an oxygen atom, a sulfur atom, an alkylene group, an alkenylene group or an alkynylene group. The suitable linker connecting the aromatic structure to the main chain can be exemplified by —C(=O)—O— or —O—C(=O)—, but is not limited thereto.

In another example, the ring structure contained in the polymer segment B of the block copolymer may comprise 1 or more, 2 or more, 3 or more, 4 or more, or 5 or more halogen atoms. In another example, the number of halogen atoms may be, for example, 30 or less, 25 or less, 20 or less, 15 or less, or 10 or less. The halogen atom may be exemplified by fluorine or chlorine, and the like, and the use of a fluorine atom may be advantageous. As described above, the polymer segment having a ring structure such as an aromatic structure containing a halogen atom can efficiently realize a phase separation structure of the block copolymer through proper interaction with other polymer segments.

Here, the polymer segment A may comprise, for example, a first monomer unit. In addition, the first monomer unit may be represented by Formula 1 below. The polymer segment may comprise the first monomer unit, that is, the unit represented by Formula 1 below as a main component.

In the present application, the fact of comprising a certain component as a main component may mean a case where the component is contained in a ratio of 60% or more, 70% or more, 80% or more, 90% or more, or 95% or more on the basis of weight, or a case where it is contained in 70 mol % or more, 80 mol % or more, 90 mol % or more, or 95 mol % or more.

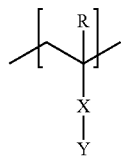

[Formula 1]

In Formula 1, R may be hydrogen or an alkyl group having 1 to 4 carbon atoms. Here, X may be a single bond, an oxygen atom, a sulfur atom, —S(=O)$_2$—, a carbonyl group, an alkylene group, an alkenylene group, an alkynylene group, —C(=O)—X$_1$— or —X$_1$—C(=O)—. Here, X$_1$ may also be an oxygen atom, a sulfur atom, —S(=O)$_2$—, an alkylene group, an alkenylene group or an alkynylene group. Here, Y may be a monovalent substituent comprising a ring structure to which the side chain having 8 or more chain-forming atoms is linked.

When the side chain is an alkyl group, the alkyl group may contain 8 or more, 9 or more, 10 or more, 11 or more, or 12 or more carbon atoms, and 30 or less, 25 or less, 20 or less or 16 or less carbon atoms.

In addition, when the side chain is an alkenyl group or an alkynyl group, it may contain 8 or more, 9 or more, 10 or more, 11 or more, or 12 or more carbon atoms, and 30 or less, 25 or less, 20 or less or 16 or less carbon atoms.

In another example, X of Formula 1 may be —C(=O)O— or —OC(=O)—.

In another example, Y in Formula 1 may be a substituent comprising the above-described side chain, where the substituent may be, for example, a substituent containing an aromatic structure having 6 to 18 carbon atoms or 6 to 12 carbon atoms. Here, the chain may be, for example, a linear alkyl group containing 8 or more, 9 or more, 10 or more, 11 or more, or 12 or more carbon atoms and 30 or less, 25 or less, 20 or less, or 16 or less carbon atoms. The chain may also be linked to the aromatic structure directly or via the above-mentioned linker.

In another example, the unit represented by Formula 1 above may be represented by Formula 1-1 below:

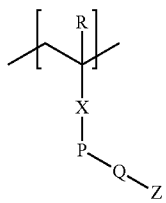

[Formula 1-1]

In Formula 1-1, R may be hydrogen or an alkyl group having 1 to 4 carbon atoms. Here, X may be —C(=O)—O—, P may be an arylene group having 6 to 12 carbon atoms, Q may be an oxygen atom, and Z may be the side chain having 8 or more chain-forming atoms.

In another example, P in Formula 1-1 may be phenylene, and in another example, Z may be a linear alkyl group having 9 to 20 carbon atoms, 9 to 18 carbon atoms, 9 to 16 carbon atoms, 10 to 16 carbon atoms, 11 to 16 carbon atoms or 12 to 16 carbon atoms. Here, when P is phenylene, Q may be connected to the para position of the phenylene. Here, the alkyl group, arylene group, phenylene group and/or side chain may be optionally substituted with one or more substituents.

The polymer segment B of the block copolymer may comprise, for example, a second monomer unit. In addition, the second monomer unit may be represented by Formula 2 below. The polymer segment may comprise the second monomer unit, that is, the unit represented by Formula 2 below as a main component.

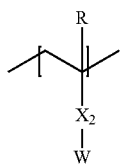

[Formula 2]

In Formula 2, R may be hydrogen or an alkyl group having 1 to 4 carbon atoms, and $X_2$ may be a single bond, an oxygen atom, a sulfur atom, —S(=O)$_2$—, an alkylene group, an alkenylene group, an alkynylene group, —C(=O)—$X_1$— or —$X_1$—C(=O)—. Here, $X_1$ may be a single bond, an oxygen atom, a sulfur atom, —S(=O)$_2$—, an alkylene group, an alkenylene group or an alkynylene group. Here, W may be an aryl group containing at least one halogen atom.

In another example, $X_2$ in Formula 2 may be a single bond or an alkylene group.

In Formula 2, the aryl group of W may be an aryl group having 6 to 12 carbon atoms or a phenyl group, and this aryl group or phenyl group may contain 1 or more, 2 or more, 3 or more, 4 or more, or 5 or more halogen atoms. Here, the number of halogen atoms may be, for example, 30 or less, 25 or less, 20 or less, 15 or less, or 10 or less. As the halogen atom, a fluorine atom may be exemplified.

In another example, the unit of Formula 2 may be represented by Formula 2-1 below.

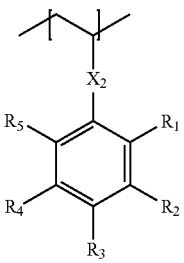

[Formula 2-1]

In Formula 2-1, $X_2$ may be a single bond, an oxygen atom, a sulfur atom, —S(=O)$_2$—, an alkylene group, an alkenylene group, an alkynylene group, —C(=O)—$X_1$— or —$X_1$—C(=O)—. Here, $X_1$ may be a single bond, an oxygen atom, a sulfur atom, —S(=O)$_2$—, an alkylene group, an alkenylene group or an alkynylene group. Here, $R_1$ to $R_5$ may be each independently hydrogen, an alkyl group, a haloalkyl group or a halogen atom, and the number of halogen atoms contained in $R_1$ to $R_5$ may be 1 or more.

In Formula 2-1, $R_1$ to $R_5$ may be each independently a hydrogen atom, an alkyl group having 1 to 4 carbon atoms, a haloalkyl group having 1 to 4 carbon atoms, or a halogen atom, where the halogen atom may be a chlorine atom or a fluorine atom.

In Formula 2-1, $R_1$ to $R_5$ may contain 2 or more, 3 or more, 4 or more, 5 or more, or 6 or more halogen atoms, and 12 or less, 8 or less, or 7 or less halogen atoms.

The method of producing the block copolymer is not particularly limited. For example, a free radical polymerization method or an LRP (living radical polymerization) method, and the like may be used. An example of the LRP method may be exemplified by an anion polymerization, an atom transfer radical polymerization method, a polymerization method by reversible addition-fragmentation chain transfer (RAFT) using an inorganic reducing agent and a reversible addition-fragmentation chain transfer agent or a method of using an organotellurium compound as an initiator, and the like.

The anion polymerization method may mean that the polymerization is performed in the presence of an inorganic acid salt, such as an alkali metal or alkaline earth metal salt, or an organoaluminum compound using an organic rare earth metal complex or an organic alkali metal compound, and the like as an initiator.

An example of the atom transfer radical polymerization method may include, for example, an atom transfer radical polymerization method (ATRP) using an atom transfer radical polymerization agent as a polymerization inhibitor, an ARGET (activators regenerated by electron transfer) atom transfer radical polymerization method (ATRP), which uses an atom transfer radical polymerization agent as a polymerization initiator, but performs polymerization under an organic or inorganic reducing agent that generates electrons, an ICAR (initiators for continuous activator regeneration) atom transfer radical polymerization method, and the like.

As the method for polymerizing a block copolymer, an appropriate method among the above-described methods may be optionally applied.

The kind of the radical initiator that can be used in the polymerization process is not particularly limited. As the radical initiator, for example, an azo-based initiator such as AIBN (azobisisobutyronitrile), ABCN (1,1'-azobis(cyclohexanecarbonitrile)) or 2,2'-azobis-(2,4-dimethylvaleronitrile) or a peroxide initiator such as BPO (benzoyl peroxide) or DTBP (di-tert-butyl peroxide), and the like can be applied.

Furthermore, depending on the kind of the component contained in the block copolymer, as a method for polymerizing the same, for example, a polymerization method without using any initiator, such as a method using thermal self-initiation of a styrenic monomer, can also be applied.

The polymerization process can be performed, for example, in the presence of a suitable solvent. In this case, the applicable solvent can be exemplified by a solvent such as methylene chloride, 1,2-dichloroethane, chlorobenzene, dichlorobenzene, benzene, toluene, anisole, acetone, chloroform, tetrahydrofuran, dioxane, monoglyme, diglyme, dimethyl formamide, dimethylsulfoxide or dimethylacetamide, but is not limited thereto. After the polymerization reaction, a non-solvent is used, whereby the polymer can be obtained by precipitation, where the usable non-solvent can be exemplified by an alcohol such as methanol, ethanol, n-propanol or isopropanol, a glycol such as ethylene glycol, an alkane such as n-hexane, cyclohexane or n-heptane, an ether such as petroleum ether, and the like, but is not limited thereto.

In the polymer synthesis field, a method of producing a polymer according to the type of a monomer forming the polymer is known, and any of the known methods may be applied upon producing the block copolymer of the present application.

In another example, the polymer composition may comprise a random copolymer together with the block copolymer. In addition, the random copolymer may comprise a monomer unit forming the polymer segment A and a monomer unit forming the polymer segment B. In other words, the random copolymer may comprise the above-described first monomer unit and the above-described second monomer unit. As described above, the first monomer unit may be represented by Formula 1 or Formula 1-1 as described above, and the second monomer unit may be represented by Formula 2 or Formula 2-1 as described above. Accordingly, the random copolymer may be a random copolymer comprising the monomer unit of Formula 1 or 1-1 and the monomer unit of Formula 2 or 2-1 as described above.

The inventors of the present invention have confirmed that when a polymer composition comprising such a random copolymer and the above-described block copolymer together is applied upon forming a polymer membrane to be described below, a block copolymer forming a self-assembled structure with a highly aligned vertical orientation structure can be obtained.

The random copolymer may comprise only the above-mentioned monomer units, or may also comprise additional units in addition to them.

In such a random copolymer, the second monomer unit (unit represented by Formula 2 or 2-1) may have a volume fraction in a range of 0.3 to 0.7, and the sum of the volume fraction of the first monomer unit (unit represented by Formula 1 or 1-1) and the volume fraction of the second monomer unit (unit represented by Formula 2 or 2-1) may be 1. In another example, the volume fraction of the second monomer unit may be about 0.35 or more and about 0.65 or less. In the case of comprising the random copolymer in which the volume fraction of the second monomer unit is adjusted as above, a self-assembled structure of a block copolymer having a more highly aligned vertical orientation structure can be formed in the polymer membrane formed of the polymer composition. If the volume fraction of the second monomer unit is less than the above range or exceeds the above range, defects in the vertical orientation of the self-assembled structure of the block copolymer may occur.

In one example, the number average molecular Weight (Mn) of the random copolymer may be in a range of, for example, 5,000 to 100,000. In another example, the molecular weight (Mn) may be, for example, 5000 or more, 7000 or more, 9000 or more, 10,000 or more, 11000 or more, or 12000 or more. In another example, the molecular weight (Mn) may be 100,000 or less, 90000 or less, 80000 or less, 70000 or less, 60000 or less, 50000 or less, 40000 or less, 30000 or less, 25,000 or less, or 24,000 or less or so. In another example, the random copolymer may have polydispersity (Mw/Mn) in a range of 1.01 to 1.80. In another example, the polydispersity may be about 1.05 or more, or about 1.1 or more. In another example, the polydispersity may be about 1.7 or less, about 1.6 or less, or about 1.5 or less. The descriptions of the molecular weight and the polydispersity are the same as those described above, and thus they will be omitted.

When such a random copolymer is mixed together with the above-described block copolymer to form a polymer membrane, it is advantageous in forming a self-assembled structure of a highly aligned block copolymer.

In addition to the first monomer unit and the second monomer unit, the random copolymer may also comprise an additional unit (third monomer unit), if necessary. Such a third monomer unit can be exemplified by a polymerization unit derived from a (meth)acrylic acid ester compound such as methyl (meth)acrylate, ethyl (meth)acrylate, n-propyl (meth)acrylate, isopropyl (meth)acrylate, n-butyl (meth)acrylate, isobutyl (meth)acrylate, t-butyl (meth)acrylate, n-hexyl (meth)acrylate or octyl (meth)acrylate, a polymerization unit derived from a vinyl pyridine such as 2-vinyl pyridine or 4-vinyl pyridine, or a polymerization unit derived from a styrenic monomer such as styrene, 4-trimethylsilylstyrene, 2,3,4,5,6-pentafluorostyrene, 3,4,5-trifluorostyrene, 2,4,6-trifluorostyrene or 4-fluorostyrene, but is not limited thereto. Furthermore, when the third unit is contained in the random copolymer, the content thereof is not particularly limited, which can be freely adjusted depending on the components of the random copolymer or the block copolymer contained in the polymer composition and the respective contents thereof.

Such a random copolymer may be prepared by a known method, and the method described in the method of polymerizing the block copolymer may be applied.

In one example, the polymer composition of the present application may comprise the random copolymer in a ratio ranging from 1 to 50 vol % based on the total volume of the block copolymer and the random copolymer. In another example, the ratio may be 1 vol % or more, 2 vol % or more, 3 vol % or more, 4 vol % or more, or 5 vol % or more, and may be 50 vol % or less, 45 vol % or less, 40 vol % or less, 35 vol % or less, or 30 vol % or less.

The present application also relates to a laminate. The laminate of the present application comprises a substrate and a polymer membrane formed on the surface of the substrate. The polymer membrane may also be formed from the polymer composition.

The laminate of the present application may be applied to a method for producing a patterned substrate to be described below. In addition, the method may be performed by a lithography method in which a directed self assembly material is applied as a template, where the directed self-assembly material may be a block copolymer contained in the polymer composition or the polymer membrane. In the production process of such a patterned substrate, the laminate of the present application makes it possible to form the self-assembled structure of the directed self-assembly material more precisely, thereby making it possible to perform patterning of the substrate precisely.

In one example, the polymer membrane may comprise the block copolymer and the random copolymer. Therefore, the block copolymer contained in the polymer membrane of the laminate may comprise a polymer segment A containing a first monomer unit and a polymer segment B having an absolute value of a surface energy difference with the polymer segment A of 10 mN/m or less and containing a second monomer unit. Also, the random copolymer contained in the polymer membrane of the laminate may comprise the first monomer unit and the second monomer unit. Furthermore, in the random copolymer contained in the polymer membrane of the laminate, the second monomer unit may have a volume fraction of 0.3 to 0.7, and the sum of the volume fractions of the first monomer unit and the second monomer unit may be 1.

The block copolymer and the random copolymer are the same as those contained in the above-described polymer composition, and thus a detailed description thereof will be omitted.

The type of the substrate included in the laminate of the present application is not particularly limited. The substrate may be etched via a mask formed by the polymer membrane in a method for producing a patterned substrate to be described below.

As such a substrate, for example, various types of substrates requiring formation of a pattern on the surface may all be used. This type of substrate may include, for example, a silicon substrate, a silicon germanium substrate, a GaAs substrate, a silicon oxide substrate, and the like. As the substrate, for example, a substrate applied to formation of finFETs (fin field effect transistors) or other electronic devices such as diodes, transistors or capacitors may be used. In addition, other materials such as ceramics may be used as the substrate depending on the application, and the types of substrates that can be applied in the present application are not limited thereto.

The block copolymer in the polymer membrane of the laminate may form a self-assembled structure. The type of the self-assembled structure formed by the block copolymer is not particularly limited, which may be a known self-assembled structure, for example, a structure such as a sphere, a cylinder or a lamella, and in one example, it may be a lamellar structure. In addition, when the self-assembled structure of the block copolymer is a lamellar or sphere structure, the lamellar structure or sphere structure may form a vertically oriented structure. When the block copolymer forms a lamellar structure in the polymer membrane of the laminate, the thickness of the polymer membrane can be adjusted in a range of 1 L to 10 L. Here, L is a pitch of a lamellar structure formed by the block copolymer. In the present application, the term pitch (L) of lamellar structure may mean a length of a pattern in the vertically oriented lamellar structure. The pitch (L) may be, for example, 1 nm or more, 2 nm or more, 3 nm or more, 4 nm or more, or 5 nm or more, and may be 50 nm or less, 45 nm or less, 40 nm or less, or 35 nm or less.

In the laminate of the present application, a neutral treatment region may not be included between the substrate and the polymer membrane. In the present application, the term neutral treatment region is a treatment region known as a so-called neutral layer (neutral brush layer) or the like in the industry, which includes all treatment regions known as being capable of achieving the vertical orientation of the block copolymer on the substrate. The neutral treatment region may mean a surface having substantially the same level of surface energy (surface tension or affinity) for each of the polymer segment A and the polymer segment B contained in the block copolymer. That is, in the laminate of the present application, the polymer membrane may be in direct contact with the substrate.

The present application also relates to a method for producing a patterned substrate using such a laminate. The patterned substrate thus produced can be used in various electronic or electronic elements, a process of forming the pattern, a recording medium such as a magnetic storage medium or a flash memory, or a biosensor, and the like.

The production method may comprise a step of coating a polymer composition comprising the above-mentioned block copolymer and random copolymer on a substrate, for example, the substrate, and annealing to form a self-assembled structure of the block copolymer.

The method of coating the polymer composition on the substrate is not particularly limited. The method may comprise, for example, a process of applying a coating liquid formed of a polymer composition comprising the block copolymer and the random copolymer to form a layer, and annealing the layer. Here, the annealing process may be a thermal annealing process or a solvent annealing process. The thermal annealing may be performed, for example, based on the phase transition temperature or the glass transition temperature of the block copolymer and/or the random copolymer, and for example, it may be performed at a temperature above the glass transition temperature or the phase transition temperature. The time for which this thermal annealing is performed is not particularly limited, and the annealing can be performed in a range of, for example, about 1 minute to 72 hours, but this can be changed as needed. The heat treatment temperature in the thermal annealing process may be, for example, about 100° C. to 250° C. or so, but this may be changed considering the block copolymer and/or the random copolymer to be used. Furthermore, the solvent annealing process may also be performed in a non-polar solvent and/or a polar solvent at a suitable room temperature for about 1 minute to 72 hours.

In one example, a neutral layer may not be present on the substrate coated with the polymer composition. The coating of the polymer composition on the substrate on which the neutral layer is not present may mean, for example, coating the polymer composition without the neutral region treatment on the surface of the silicon substrate or the like as described above. Therefore, the production method of the present application may comprise a process of applying a coating liquid formed of the polymer composition comprising the block copolymer and the random copolymer as described above on the substrate without the neutral region treatment to form a layer, and annealing the layer. In addition, the neutral layer may have the same meaning as the neutral treatment region as described above. The method for producing a patterned substrate of the present application forms a polymer membrane comprising the block copolymer and the random copolymer as described above even on the substrate on which a neutral layer is not formed and allows the block copolymer to form a self-assembled structure, whereby the self-assembled structure of the block copolymer can also form a vertically oriented lamellar structure without the neutral treatment and thus the highly patterned substrate can be produced.

In one example, in the block copolymer and the random copolymer to be applied to the method for producing a patterned substrate of the present application, the ratio of the random copolymer may be in a range of 1 to 50 vol % based on 100 vol % of the total of the block copolymer and the random copolymer. The ratio of the random copolymer may be 1 vol % or more, 2 vol % or more, 3 vol % or more, 4 vol % or more, or 5 vol % or more, and may be 50 vol % or less, 45 vol % or less, 40 vol % or less, 35 vol % or less, or 30 vol % or less, based on 100 vol % of the total of the block copolymer and the random copolymer.

The patterned substrate production method may further perform a step of selectively removing any one of the polymer segments of the block copolymer that the self-assembled structure is formed as above. For example, it may comprise a process of selectively removing the polymer segment A or B of the block copolymer from the laminate. In addition, the production method may comprise selectively removing any one or more polymer segments of the block copolymer and then etching the substrate. In this way, it is possible to form, for example, a nanoscale fine pattern. In addition, various types of patterns such as nano-rods or nano-holes can be formed through the above-described method depending on the shape of the block copolymer in the polymer membrane. If necessary, a copolymer different from the block copolymer or a homopolymer, and the like may be mixed for pattern formation.

In the above method, the method of selectively removing any one polymer segment of the block copolymer is not particularly limited, and for example, a method of removing a relatively soft polymer segment by irradiating the polymer membrane with an appropriate electromagnetic wave, for example, ultraviolet or the like, can be used. In this case, the ultraviolet irradiation condition is determined according to the type of the polymer segment of the block copolymer, and the method can be performed, for example, by being irradiated with ultraviolet having a wavelength of about 254 nm for 1 minute to 60 minutes.

Following the ultraviolet irradiation, a step of treating the polymer membrane with an acid or the like to further remove the segment decomposed by ultraviolet may also be performed.

The step of etching the substrate using the polymer membrane in which the polymer segments are selectively removed as a mask is not particularly limited, which may be performed, for example, through a reactive ion etching step using $CF_4/Ar$ ions or the like and following this process, a step of removing the polymer membrane from the substrate by an oxygen plasma treatment or the like may also be performed.

Advantageous Effects

The present application relates to a laminate. The present application can form a highly aligned block copolymer without orientation defects, coordination number defects distance defects and the like on a substrate, thereby providing a laminate which can be effectively applied to the production of various patterned substrates, and a method for producing a patterned substrate using the same.

BRIEF DESCRIPTION OF DRAWINGS

FIG. 1 shows the GIWAXS analysis results of the monomer (A) synthesized in Preparation Example 1.

FIG. 2 is an SEM photograph of the polymer membrane prepared in Example 1.

FIG. 3 is a SEM photograph of the polymer membrane prepared in Example 2.

FIG. 4 is a SEM photograph of the polymer membrane prepared in Example 3.

FIG. 5 is a SEM photograph of the polymer membrane prepared in Example 4.

FIG. 6 is a SEM photograph of the polymer membrane prepared in Example 5.

FIG. 7 is an SEM photograph of the polymer membrane prepared in Comparative Example 1.

FIG. 8 is an SEM photograph of the polymer membrane prepared in Comparative Example 2.

FIG. 9 is a SEM photograph of the polymer membrane prepared in Comparative Example 3.

FIG. 10 is an SEM photograph of the polymer membrane prepared in Comparative Example 4.

MODE FOR INVENTION

Hereinafter, the present application will be described in detail by way of examples and comparative examples, but the scope of the present application is not limited by the following examples.

1. NMR Measurement

NMR analyses were performed at room temperature using an NMR spectrometer including a Varian Unity Inova (500 MHz) spectrometer with a triple resonance 5 mm probe. An analyte was diluted in a solvent for NMR measurement ($CDCl_3$) to a concentration of about 10 mg/ml, and chemical shifts were expressed in ppm.

<Application Abbreviation> br=broad signal, s=singlet, d=doublet, dd=double doublet, t=triplet, dt=double triplet, q=quartet, p=quintet, m=multiplet.

2. GPC (Gel Permeation Chromatograph)

The number average molecular weight (Mn) and the molecular weight distribution were measured using GPC (gel permeation chromatography) according to the following procedure.

(1) Into a 5 mL vial, an analyte such as block copolymers of Examples or Comparative Examples or a macro initiator is put and diluted in THF (tetrahydrofuran) to be a concentration of about 1 mg/mL or so.

(2) A standard sample for calibration and a sample to be analyzed are filtered through a syringe filter (pore size: 0.45 μm).

(3) The GPC analysis is performed after injecting the filtered standard sample and analytical sample into the GPC apparatus.

As the analytical program, ChemStation from Agilent Technologies was used, and the elution time of the sample was compared with the calibration curve to obtain the weight average molecular weight (Mw) and the number average molecular weight (Mn), respectively, and the molecular weight distribution (PDI) was calculated by the ratio (Mw/Mn) thereof. The measurement conditions of GPC are as follows.

<GPC Measurement Conditions>

Instrument: 1200 series from Agilent Technologies

Column: using PLgel mixed B from Polymer laboratories

Solvent: THF

Column temperature: 35° C.

Sample concentration: 1 mg/mL, 200 μL injection

Standard samples: Polystyrene (Mp: 3900000, 723000, 316500, 52200, 31400, 7200, 3940, 485)

3. GISAXS (Grazing Incidence Small Angle X-Ray Scattering)

The grazing incidence small angle X-ray scattering (GISAXS) analysis was performed using a Pohang accelerator 3C beamline according to the following procedure.

(1) The block copolymer to be analyzed is diluted in fluorobenzene to a solid concentration of about 0.7 wt % to prepare a coating liquid.

(2) The coating liquid is spin-coated on a base material to a thickness of about 5 nm. At this time, the coating area is adjusted to 2.25 cm$^2$ or so (width: 1.5 cm, height: 1.5 cm).

(3) After the coating, it is dried at room temperature for about 1 hour.

(4) The dried collating liquid is subjected to thermal annealing again at about 160° C. for about 1 hour to form a polymer membrane in which the phase separation structure of the block copolymer to be analyzed is induced.

(5) After an X-ray is incident on the formed polymer membrane at an incident angle in a range of about 0.12 degrees to 0.23 degrees corresponding to the angle between the critical angle of the membrane and the critical angle of the base material, an X-ray diffraction pattern, which is scattered from the membrane to a detector (2D marCCD) and exited, is obtained. At this time, when the distance from the membrane to the detector was within a range of about 2 m to 3 m, it was confirmed that the self-assembly pattern formed on the membrane was well observed.

As the base material, a base material having a hydrophilic surface (a silicon substrate treated with a piranha solution and having a room temperature wetting angle of about 5 degrees to pure water) or a base material having a hydrophobic surface (a silicon substrate treated with HMDS (hexamethyldisilazane) and having a room temperature wetting angle of about 60 degrees to pure water) was used.

4. XRD Analysis

The XRD analysis was performed by transmitting X rays to a sample at a Pohang accelerator 4C beamline to measure the scattering intensity according to the scattering vector (q). As the sample, a polymer in a powder state dried by purifying a synthesized polymer without special pretreatment and then maintaining it in a vacuum oven for one day or so, was placed in a cell for XRD measurement and used. Upon the XRD pattern analysis, an X-ray with a vertical size of 0.023 mm and a horizontal size of 0.3 mm was used and a 2D marCCD was used as a detector. A 2D diffraction pattern scattered and exited was obtained as an image. The obtained diffraction pattern was analyzed by a numerical analytical method to which a least-square method was applied to obtain information such as a scattering vector and a half-value width. Upon the analysis, an origin program was applied, and the profile of the XRD patterns was subjected to Gaussian fitting in a state where a portion showing the smallest intensity in the XRD diffraction patterns was taken as a baseline and the intensity in the above was set to zero, and then the scattering vector and the half-value width were obtained from the fitted results. The R square was set to be at least 0.96 or more upon Gaussian fitting.

5. Measurement of Surface Energy

The surface energy was measured using a drop shape analyzer (DSA100 product from KRUSS) according to the following procedure.

(1) A coating liquid is prepared by diluting the substance (polymer), which is measured, in fluorobenzene to a solid concentration of about 2 wt %.

(2) The prepared coating liquid is spin-coated on a silicon wafer to a thickness of about 50 nm and a coating area of 4 cm$^2$ (width: 2 cm, height: 2 cm) to form a coating layer.

(3) The coating layer was dried at room temperature for about 1 hour and then subjected to thermal annealing at about 160° C. for about 1 hour.

(4-1) The process of dropping the deionized water whose surface tension is known on the membrane after the thermal annealing and obtaining the contact angle thereof is repeated five times to obtain an average value of the obtained five contact angle values.

(4-2) In the same manner, the process of dropping the diiodomethane whose surface tension is known on the membrane after the thermal annealing and obtaining the contact angle thereof is repeated five times to obtain an average value of the obtained five contact angle values.

(5) The surface energy is obtained by substituting the value (Strom value) regarding the solvent surface tension by the Owens-Wendt-Rabel-Kaelble method using the average values of the contact angles for the deionized water and diiodomethane obtained in Steps (4-1) and (4-2) above.

The numerical value of the surface energy for each polymer segment of the block copolymer was obtained for a homopolymer made of only the monomer forming the polymer segment by the above-described method.

6. GIWAXS (Grazing Incidence Wide Angle X-Ray Scattering)

The grazing incidence wide angle X-ray scattering (GIWAXS) analysis was performed using a Pohang accelerator 3C beamline according to the following procedure.

(1) The block copolymer to be analyzed is diluted in toluene to a solid concentration of about 1 wt % to prepare a coating liquid.

(2) The coating liquid was spin-coated on the substrate to a thickness of about 30 nm. At this time, the coating area is adjusted to about 2.25 cm$^2$ (width: 1.5 cm, height: 1.5 cm).

(3) The coated coating solution was dried at room temperature for about 1 hour, and then subjected to thermal annealing at a temperature of about 160° C. for about 1 hour to form a polymer membrane.

(4) After an X-ray is incident on the membrane at an incident angle in a range of about 0.12 degrees to 0.23 degrees corresponding to the angle between the critical angle of the membrane and the critical angle of the base material, an X-ray diffraction pattern, which is scattered from the membrane to a detector (2D marCCD) and exited, is obtained. At this time, it was confirmed that the crystal or liquid crystal structure formed on the membrane was well observed when the distance from the membrane to the detector was within the range of about 0.1 m to 0.5 m.

As the base material, a base material having a hydrophilic surface (a silicon substrate treated with a piranha solution and having a room temperature wetting angle of about 5 degrees to pure water) was used.

(5) In the GIWAXS spectrum, the scattering intensity in the azimuthal angle range of −90 degrees to 90 degrees of the diffraction pattern in the range of 12 nm$^{-1}$ to 16 nm$^{-1}$ (azimuthal angle when the upward direction of the diffraction pattern (out-of-plane diffraction pattern) is set as 0 degrees) is plotted, and the half-value width is obtained from the graph through Gauss fitting. At this time, when half of the peak was observed upon Gauss fitting, twice the value of the obtained half-value width (FWHM) was defined as the half-value width of the peak.

7. DSC Analysis

The DSC analysis was performed using PerkinElmer DSC800 equipment according to the following procedure.

(1) The sample to be analyzed is heated at a rate of 10° C. per minute from 25° C. to 200° C. under nitrogen atmosphere using the above equipment.

(2) Subsequently, the sample to be analyzed is cooled from 200° C. to −80° C. at a rate of −10° C. per minute.

(3) The sample to be analyzed is again raised from −80° C. to 200° C. at a rate of 10° C. per minute.

(4) An endothermic curve according to the above procedure is obtained.

(5) At this time, the obtained endothermic curve is analyzed to obtain a temperature (melting transition temperature, Tm) indicating a melting transition peak or a temperature (isotropic transition temperature, Ti) indicating an isotropic transition peak, and the area of the peak is obtained.

Here, the temperature was defined as the temperature corresponding to the apex of each peak. Furthermore, the area per unit mass of each peak was defined as the value obtained by dividing the area of each peak by the mass of the sample, and this calculation was calculated using the program provided by the DSC equipment.

8. Analysis of Volume Fraction

The volume fractions of a block copolymer and a random copolymer were calculated based on the NMR measurement results. Specifically, the volume fractions of the block copolymer and the random copolymer were calculated using Equation 3 below.

Volume fraction $X = 1/\{1 + (D \times M)/(K \times L)\}$ [Equation 3]

The variables D, M, K and L applied to Equation 3 can be obtained by the following methods, respectively.

D can be obtained by placing a sample to be analyzed (a homopolymer made only of the monomer forming the first block or a homopolymer made only of the monomer forming the second block) in ethanol (a solvent in which the mass and density in air are known), obtaining the density of each block through the mass, and calculating their ratios.

Also, M can be obtained by the molecular weight of the monomer forming each block of the block copolymer.

Furthermore, L can be obtained by the ratio of the number of hydrogen atoms of the monomer forming each block of the block copolymer, and for example, can be obtained from the structural formula of the monomer constituting each block copolymer.

Finally, K can be calculated through the area of the spectrum obtained by the NMR measurement method as described above. At this time, in this case, when the peaks derived from the respective blocks of the block copolymer do not overlap, the area of the peak derived from each block is obtained, and K can be obtained through the ratio.

However, when there is a portion where peaks derived from each block of the block copolymer overlap, the K should be obtained in consideration of this. In this case, a method of obtaining the K value in consideration of the superposition or the like is known, and for example, it can be obtained by applying an NMR analysis program such as a MestReC program, or the like.

Preparation Example 1. Synthesis of monomer (A)

A monomer (DPM-C12) of Formula A below was synthesized in the following manner.

(1) Hydroquinone (10.0 g, 94.2 mmol) and 1-bromododecane (23.5 g, 94.2 mmol) are placed in a 250 mL flask, dissolved in 100 mL of acetonitrile, and then an excess amount of potassium carbonate is added thereto and reacted at 75° C. for about 48 hours under a nitrogen condition.

(2) After the reaction, the remaining potassium carbonate is filtered off and the acetonitrile used in the reaction is also removed.

(3) A mixed solvent of DCM (dichloromethane) and water is added thereto to work up the mixture, and the separated organic layers are collected and passed through $MgSO_4$ to be dehydrated.

(4) Subsequently, the target product (4-dodecyloxyphenol) (9.8 g, 35.2 mmol) in a white solid phase is obtained using dichloromethane in column chromatography. At this time, the yield of the obtained target product was about 37%.

<NMR analysis results>

$^1$H-NMR (CDCl$_3$): δ6.77 (dd, 4H); δ4.45 (s, 1H); δ3.89 (t, 2H); δ1.75 (p, 2H); δ1.43 (p, 2H); δ1.33-1.26 (m, 16H); δ0.88 (t, 3H).

(5) The synthesized 4-docecyloxyphenol (9.8 g, 35.2 mmol), methacrylic acid (6.0 g, 69.7 mmol), DCC (dicyclohexylcarbodiimide) (10.8 g, 52.3 mmol) and DMAP (p-dimethylaminopyridine) (1.7 g, 13.9 mmol) are placed in the flask and 120 mL of methylene chloride is added thereto, and then reacted at room temperature for 24 hours under nitrogen.

(6) After completion of the reaction, the salt (urea salt) produced during the reaction and methylene chloride are removed with a filter.

(7) Impurities are removed using hexane and DCM (dichloromethane) as the mobile phase in column chromatography and the product obtained again is recrystallized in a mixed solvent of methanol and water (1:1 mix) to obtain the target product (7.7 g, 22.2 mmol) in a white solid phase. At this time, the yield of the obtained target product was about 63%.

<NMR Analysis Results>

$^1$H-NMR (CDCl$_3$): δ7.02 (dd, 2H); δ6.89 (dd, 2H); δ6.32 (dt, 1H); δ5.73 (dt, 1H); δ3.94 (t, 2H); δ2.05 (dd, 3H); δ1.76 (p, 2H); δ1.43 (p, 2H); 1.34-1.27 (m, 16H); δ0.88 (t, 3H).

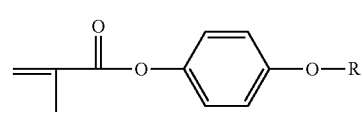

[Formula A]

In Formula A, R is a linear alkyl group having 12 carbon atoms.

GIWAXS, XRD and DSC Analyses

A homopolymer was prepared using the monomer (A) of Preparation Example 1, and GIWAXS and DSC were analyzed for the prepared homopolymer. Here, the homopolymer was prepared by a method of synthesizing a macromonomer using the monomer (A) in the following examples.

FIG. 1 shows the results of GIWAXS analysis of the homopolymer. In FIG. 1, R square was about 0.264 upon Gauss fitting. As a result of the DSC analysis for the homopolymer, the corresponding polymer showed a melting temperature of about −3° C. and an isotropic transition temperature of about 15° C. Also, the ratio (M/I) of the area (M) of the melting transition peak to the area (I) of the isotropic transition peak in the DSC analysis of the homopolymer was about 3.67, the half-value width of the peak in an azimuthal angle of −90 degrees to 70 degrees of the diffraction pattern of the scattering vector in a range of 12 nm$^{-1}$ to 16 nm$^{-1}$ in GIWAXS was about 48 degrees, and the half-value width of the peak in an azimuthal angle of 70 degrees to 90 degrees of the diffraction pattern of the scattering vector in a range of 12 nm$^{-1}$ to 16 nm$^{-1}$ in GIWAXS was about 58 degrees. Furthermore, in the X-ray diffraction analysis (XRD), a peak having a half-value width of about 0.57 nm$^{-1}$ or so was observed at a scattering vector value of 1.96 nm$^{-1}$.

Preparation Example 2. Synthesis of Block Copolymer (B)

The block copolymer (B) was synthesized in the following manner.

(1) 2.0 g of the monomer (A) of Preparation Example 1, 64 mg of cyanoisoproyl dithiobenzoate as an RAFT (reversible addition-fragmentation chain transfer) reagent, 6 mg of AIBN (azobisisobutyronitrile) as a radical initiator and 5.34 mL of benzene are placed in a 10 mL Schlenk flask and stirred at room temperature for 30 minutes under a nitrogen atmosphere.

(2) An RAFT (reversible addition-fragmentation chain transfer) polymerization reaction is performed at 70° C. for 4 hours.

(3) After the polymerization, the reaction solution is precipitated in 250 mL of methanol as an extraction solvent, and then filtered under reduced pressure and dried to prepare a pink macro initiator.

At this time, the yield of the macro initiator was about 82.6 wt %, and the number average molecular weight (Mn) and the molecular weight distribution (Mw/Mn) were 4,400 and 1.16, respectively.

(4) 0.3 g of the macro initiator, 2.7174 g of a pentafluorostyrene monomer and 1.306 mL of benzene are placed in a 10 mL Schlenk flask and stirred at room temperature for 30 minutes under a nitrogen atmosphere.

(5) An RAFT (reversible addition-fragmentation chain transfer) polymerization reaction is performed at 115° C. for 6 hours.

(6) After the polymerization, the reaction solution is precipitated in 250 mL of methanol, which is an extraction solvent, and then filtered and dried under reduced pressure to obtain a pale pink block copolymer (B). At this time, the yield of the block copolymer was about 18 wt %, and the number average molecular weight (Mn) and the molecular weight distribution (Mw/Mn) were 14,400 and 1.12, respectively. The block copolymer comprised a polymer segment A, which was derived from the monomer (A) of Preparation Example 1 and had 12 chain-forming atoms (the number of carbon atoms of R in Formula A), and a polymer segment B derived from the pentafluorostyrene monomer. The volume fraction of the polymer segment A in the block copolymer was about 0.41 or so, and the volume fraction of the polymer segment B was about 0.59 or so. The surface energy and density of the polymer segment A of the block copolymer were 30.83 mN/m and 1 g/cm$^3$, respectively, and the surface energy and density of the polymer segment B were 24.4 mN/m and 1.57 g/cm$^3$, respectively. Also, the result calculated by substituting the number (12) of chain-forming atoms in the polymer segment A of the block copolymer and the scattering vector value (q) in which the peak having the largest peak area was identified in the scattering vector range of 0.5 nm$^{-1}$ to 10 nm$^{-1}$ upon the X-ray diffraction analysis into the equation nq/(2×π), respectively, was about 3.75.

Preparation Example 3. Synthesis of Block Copolymer (C)

The block copolymer (C) was synthesized in the following manner.

(1) 2.0 g of the monomer (A) of Preparation Example 1, 67 mg of cyanoisoproyl dithiobenzoate as an RAFT (reversible addition-fragmentation chain transfer) reagent, 7 mg of AIBN (azobisisobutyronitrile) as a radical initiator and 5.37 mL of anisole are placed in a 10 mL Schlenk flask and stirred at room temperature for 30 minutes under a nitrogen atmosphere.

(2) An RAFT (reversible addition-fragmentation chain transfer) polymerization reaction is performed at 70° C. for 4 hours.

(3) After the polymerization, the reaction solution is precipitated in 250 mL of methanol as an extraction solvent, and then filtered under reduced pressure and dried to prepare a pink macro initiator.

The yield of the macro initiator was about 81.3 wt %, and the number average molecular weight (Mn) and the molecular weight distribution (Mw/Mn) were 9,100 and 1.17, respectively.

(4) 0.3 g of the macro initiator, 2.74 g of a pentafluorostyrene monomer and 1.352 mL of anisole are placed in a 10 mL Schlenk flask and stirred at room temperature for 30 minutes under a nitrogen atmosphere.

(5) An RAFT (reversible addition-fragmentation chain transfer) polymerization reaction is performed at 115° C. for 4 hours.

(6) After the polymerization, the reaction solution is precipitated in 250 mL of methanol, which is an extraction solvent, and then filtered and dried under reduced pressure to obtain a pale pink block copolymer (C). The yield of the block copolymer was about 17 wt %, and the number average molecular weight (Mn) and the molecular weight distribution (Mw/Mn) were 24,500 and 1.12, respectively. The block copolymer comprised a polymer segment A, which was derived from the monomer (A) of Preparation Example 1 and had 12 chain-forming atoms (the number of carbon atoms of R in Formula A), and a polymer segment B derived from the pentafluorostyrene monomer. Here, the volume fraction of the polymer segment A was about 0.48 or so, and the volume fraction of the polymer segment B was about 0.52 or so. The surface energy and density of the polymer segment A of the block copolymer were 30.83 mN/m and 1 g/cm$^3$, respectively, and the surface energy and density of the polymer segment B were 24.4 mN/m and 1.57 g/cm$^3$, respectively. Also, the result calculated by substituting the number (12) of chain-forming atoms in the polymer segment A of the block copolymer and the scattering vector value (q) in which the peak having the largest peak area was identified in the scattering vector range of 0.5 nm$^{-1}$ to 10 nm$^{-1}$ upon the X-ray diffraction analysis into the equation nq/(2×π), respectively, was about 3.75.

Preparation Example 4. Synthesis of Random Copolymer (D)

The random copolymer (D) was synthesized in the following manner.

(1) 0.970 g of the monomer (A) of Preparation Example 1, 1.359 g of pentafluorostyrene, 6.6 mg of AIBN (azobisisobutyronitrile) as a radical initiator, 33.0 mg of an RAFT (reversible addition-fragmentation chain transfer) reagent (2-hydroxyethyl 2-(((dodecylthio)carbonothioyl)thio)-2-methylpropanoate), and 2.23 mL of anisole are placed in a 10 mL Schlenk flask and stirred at room temperature for 30 minutes under a nitrogen atmosphere.

(2) A radical polymerization reaction is performed at 70° C. for 12 hours.

(3) After the polymerization, the reaction solution is precipitated in 250 mL of methanol as an extraction solvent, and then filtered under reduced pressure, and then dried to obtain a random copolymer.

Here, the number average molecular weight (Mn) and the molecular weight distribution (Mw/Mn) of the random copolymer were 17,100 and 1.28, respectively. Also, in the random copolymer, the volume fraction of the monomer unit of Preparation Example 1 was 0.50, and the volume fraction of the pentafluorostyrene unit was about 0.50.

Preparation Example 5. Synthesis of Random Copolymer (E)

The random copolymer (E) was synthesized in the following manner.

(1) 0.700 g of the monomer (A) of Preparation Example 1, 2.194 g of pentafluorostyrene, 6.6 mg of AIBN (azobisisobutyronitrile) as a radical initiator, 33.0 mg of an RAFT (reversible addition-fragmentation chain transfer) reagent (2-hydroxyethyl 2-(((dodecylthio)carbonothioyl)thio)-2-methylpropanoate), and 2.23 mL of anisole are placed in a 10 mL Schlenk flask and stirred at room temperature for 30 minutes under a nitrogen atmosphere.

(2) A radical polymerization reaction is performed at 70° C. for 12 hours.

(3) After the polymerization, the reaction solution is precipitated in 250 mL of methanol as an extraction solvent, and then filtered under reduced pressure, and then dried to obtain a random copolymer.

Here, the number average molecular weight (Mn) and the molecular weight distribution (Mw/Mn) of the random copolymer were 12,700 and 1.16, respectively. Also, in the random copolymer, the volume fraction of the monomer unit of Preparation Example 1 was 0.37, and the volume fraction of the pentafluorostyrene unit was about 0.63.

Preparation Example 6. Synthesis of Random Copolymer (F)

The random copolymer (F) was synthesized in the following manner.

(1) 1.259 g of the monomer (A) of Preparation Example 1, 1.254 g of pentafluorostyrene, 6.6 mg of AIBN (azobisisobutyronitrile) as a radical initiator, 33.0 mg of an RAFT (reversible addition-fragmentation chain transfer) reagent (2-hydroxyethyl 2-(((dodecylthio)carbonothioyl)thio)-2-methylpropanoate), and 2.553 mL of anisole are placed in a 10 mL Schlenk flask and stirred at room temperature for 30 minutes under a nitrogen atmosphere.

(2) A radical polymerization reaction is performed at 70° C. for 12 hours.

(3) After the polymerization, the reaction solution is precipitated in 250 mL of methanol as an extraction solvent, and then filtered under reduced pressure, and then dried to obtain a random copolymer.

Here, the number average molecular weight (Mn) and the molecular weight distribution (Mw/Mn) of the random copolymer were 12,400 and 1.17, respectively. Also, in the random copolymer, the volume fraction of the monomer unit of Preparation Example 1 was 0.65, and the volume fraction of the pentafluorostyrene unit was about 0.35.

Preparation Example 7. Synthesis of Random Copolymer (G)

The random copolymer (G) was synthesized in the following manner.

(1) 0.560 g of the monomer (A) of Preparation Example 1, 2.664 g of pentafluorostyrene, 6.6 mg of AIBN (azobisisobutyronitrile) as a radical initiator, 33.0 mg of an RAFT (reversible addition-fragmentation chain transfer) reagent (2-hydroxyethyl 2-(((dodecylthio)carbonothioyl)thio)-2-methylpropanoate), and 3.234 mL of anisole are placed in a 10 mL Schlenk flask and stirred at room temperature for 30 minutes under a nitrogen atmosphere.

(2) A radical polymerization reaction is performed at 70° C. for 12 hours.

(3) After the polymerization, the reaction solution is precipitated in 250 mL of methanol as an extraction solvent, and then filtered under reduced pressure, and then dried to obtain a random copolymer.

Here, the number average molecular weight (Mn) and the molecular weight distribution (Mw/Mn) of the random copolymer were 12,000 and 1.18, respectively. Also, in the random copolymer, the volume fraction of the monomer unit of Preparation Example 1 was 0.29, and the volume fraction of the pentafluorostyrene unit was about 0.71.

Preparation Example 8. Synthesis of Random Copolymer (H)

The random copolymer (H) was synthesized in the following manner.

(1) 4.449 g of the monomer (A) of Preparation Example 1, 2.022 g of pentafluorostyrene, 6.6 mg of AIBN (azobisisobutyronitrile) as a radical initiator, 33.0 mg of an RAFT (reversible addition-fragmentation chain transfer) reagent (2-hydroxyethyl 2-(((dodecylthio)carbonothioyl)thio)-2-methylpropanoate), and 6.510 mL of anisole are placed in a 10 mL Schlenk flask and stirred at room temperature for 30 minutes under a nitrogen atmosphere.

(2) A radical polymerization reaction is performed at 70° C. for 12 hours.

(3) After the polymerization, the reaction solution is precipitated in 250 mL of methanol as an extraction solvent, and then filtered under reduced pressure, and then dried to obtain a random copolymer.

Here, the number average molecular weight (Mn) and the molecular weight distribution (Mw/Mn) of the random copolymer were 23,400 and 1.34, respectively. Also, in the random copolymer, the volume fraction of the monomer unit of Preparation Example 1 was 0.73, and the volume fraction of the pentafluorostyrene unit was about 0.27.

Example 1

A polymer composition was prepared by blending the block copolymer (B) of Preparation Example 2 and the random copolymer (D) of Preparation Example 4 on a silicon wafer substrate such that the volume fraction of the random copolymer of Preparation Example 4 was about 5 vol % relative to the total volume of the block copolymer and the random copolymer. A coating solution prepared by diluting the polymer composition to a solid content concentration of about 0.6 wt % in fluorobenzene was spin-coated on the substrate to a thickness of about 25 nm and dried at room temperature for about 1 hour. Subsequently, the coating liquid was subjected to thermal annealing at a temperature of about 180° C. for about 1 hour to form a polymer membrane. A scanning electron microscope (SEM) image of the polymer membrane was taken and shown in FIG. 2. The block copolymer in the polymer membrane formed a vertically oriented lamellar phase, where the pitch thereof was about 11 nm or so. From FIG. 2, it can be confirmed that the block copolymer can form a highly aligned vertically oriented lamellar pattern in the polymer membrane produced by the polymer composition of the present application.

Example 2

A polymer membrane was formed in the same manner as in Example 1, except that a polymer composition was prepared by blending the block copolymer (B) of Preparation Example 2 and the random copolymer (D) of Preparation Example 4 on a silicon wafer substrate such that the volume fraction of the random copolymer (D) of Preparation Example 4 was about 15 vol % relative to the total volume of the block copolymer and the random copolymer. A scanning electron microscope (SEM) image of the polymer membrane was taken and shown in FIG. 3. The block copolymer in the polymer membrane formed a vertically oriented lamellar phase, where the pitch thereof was about 11 nm or so. From FIG. 3, it can be confirmed that the block copolymer can form a highly aligned vertically oriented lamellar pattern in the polymer membrane produced by the polymer composition of the present application.

Example 3

A polymer composition was prepared by blending the block copolymer (C) of Preparation Example 3 and the random copolymer (D) of Preparation Example 4 on a silicon wafer substrate such that the volume fraction of the random copolymer of Preparation Example 4 was about 15 vol % relative to the total volume of the block copolymer and the random copolymer. A coating solution prepared by diluting the polymer composition to a solid content concentration of about 0.8 wt % in fluorobenzene was spin-coated on the substrate to a thickness of about 30 nm and dried at room temperature for about 1 hour. Subsequently, the coating liquid was subjected to thermal annealing at a temperature of about 230° C. for about 1 hour to form a polymer membrane. A scanning electron microscope (SEM) image of the polymer membrane was taken and shown in FIG. 4.

The block copolymer in the polymer membrane formed a vertically oriented lamellar phase, where the pitch thereof was about 17 nm or so. From FIG. 4, it can be confirmed that the block copolymer can form a highly aligned vertically oriented lamellar pattern in the polymer membrane produced by the polymer composition of the present application.

Example 4

A polymer membrane was formed in the same manner as in Example 1, except that a polymer composition was prepared by blending the block copolymer (B) of Preparation Example 2 and the random copolymer (E) of Preparation Example 5 on a silicon wafer substrate such that the volume fraction of the random copolymer of Preparation Example 5 was about 10 vol % relative to the total volume of the block copolymer and the random copolymer. A scanning electron microscope (SEM) image of the polymer membrane was taken and shown in FIG. 5. The block copolymer in the polymer membrane formed a vertically oriented lamellar phase, where the pitch thereof was about 11 nm or so. From FIG. 5, it can be confirmed that the block copolymer can form a highly aligned vertically oriented lamellar pattern in the polymer membrane produced by the polymer composition of the present application.

Example 5

A polymer membrane was formed in the same manner as in Example 1, except that a polymer composition was prepared by blending the block copolymer (B) of Preparation Example 2 and the random copolymer (F) of Preparation Example 6 on a silicon wafer substrate such that the volume fraction of the random copolymer of Preparation Example 6 was about 10 vol % relative to the total volume of the block copolymer and the random copolymer. A scanning electron microscope (SEM) image of the polymer membrane was taken and shown in FIG. 6. The block copolymer in the polymer membrane formed a vertically oriented lamellar phase, where the pitch thereof was about 11 nm or so. From FIG. 6, it can be confirmed that the block copolymer can form a highly aligned vertically oriented lamellar pattern in the polymer membrane produced by the polymer composition of the present application.

Comparative Example 1

A polymer membrane was formed in the same manner as in Example 1, except that the polymer composition containing the block copolymer (B) of Preparation Example 2 alone was prepared without containing the random copolymer. A scanning electron microscope (SEM) image of the polymer membrane was taken and shown in FIG. 7. From FIG. 7, it can be seen that in the polymer membrane of Comparative Example 1, more horizontal orientation defects are observed in the self-assembled structure formed by the block copolymer, as compared with the polymer membranes of Example 1 and Example 2.

Comparative Example 2

A polymer membrane was formed in the same manner as in Example 3, except that the polymer composition containing the block copolymer (C) of Preparation Example 3 alone was prepared without containing the random copolymer. A scanning electron microscope (SEM) image of the polymer membrane was taken and shown in FIG. 8. From FIG. 8, it can be seen that in the polymer membrane of Comparative Example 2, more horizontal orientation defects are observed in the self-assembled structure formed by the block copolymer, as compared with the polymer membrane of Example 3.

Comparative Example 3

A polymer membrane was formed in the same manner as in Example 1, except that a polymer composition was prepared by blending the block copolymer (B) of Preparation Example 2 and the random copolymer (G) of Preparation Example 7 on a silicon wafer substrate such that the volume fraction of the random copolymer (G) of Preparation Example 7 was about 10 vol % relative to the total volume of the block copolymer and the random copolymer. A scanning electron microscope (SEM) image of the polymer membrane was taken and shown in FIG. 9. According to FIG. 9, it can be confirmed that the block copolymer in the polymer membrane is not vertically oriented to the bottom of the substrate, and U-shaped defects exist in the polymer membrane.

Comparative Example 4

A polymer membrane was formed in the same manner as in Example 1, except that a polymer composition was prepared by blending the block copolymer (B) of Preparation Example 2 and the random copolymer (H) of Preparation Example 8 on a silicon wafer substrate such that the volume fraction of the random copolymer (H) of Preparation Example 9 was about 10 vol % relative to the total volume of the block copolymer and the random copolymer. A scanning electron microscope (SEM) image of the polymer membrane was taken and shown in FIG. 10. According to FIG. 10, it can be confirmed that the block copolymer in the polymer membrane is not vertically oriented to the bottom of the substrate, and horizontal orientation defects exist in the polymer membrane.

The invention claimed is:

1. A polymer composition comprising:
a block copolymer which comprises a polymer segment A containing a first monomer unit and a polymer segment B having an absolute value of a surface energy difference with the polymer segment A of 10 mN/m or less and the polymer segment B containing a second monomer unit; and
a random copolymer containing the first monomer unit and the second monomer unit, wherein the second monomer unit in the random copolymer has a volume fraction of 0.3 to 0.7, and a sum of volume fractions of the first monomer unit and the second monomer unit in the random copolymer is 1,
wherein the random copolymer is contained in a ratio of 1 vol % to 50 vol % based on a total volume of the block copolymer and the random copolymer, and
wherein the first monomer unit is a unit represented by formula 1 below:

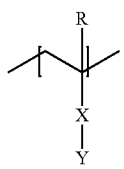

[Formula 1]

wherein, R is hydrogen or an alkyl group having 1 to 4 carbon atoms, X is a single bond, an oxygen atom, a sulfur atom, —S(=O)$_2$—, a carbonyl group, an alkylene group, an alkenylene group, —C(=O)—X$_1$— or —X$_1$—C(=O)—, where X$_1$ is an oxygen atom, a sulfur atom, an alkylene group, an alkenylene group or an alkynylene group, and Y is a monovalent substituent comprising a ring structure to which a side chain having 8 or more chain-forming atoms is linked,
wherein the second monomer unit is a unit represented by formula 2 below:

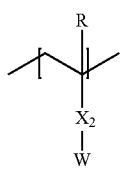

[Formula 2]

wherein, R is hydrogen or an alkyl group having 1 to 4 carbon atoms, X$_2$ is a single bond, an oxygen atom, a sulfur atom, —S(=O)$_2$—, an alkylene group, an alkenylene group, —C(=O)—X$_1$— or —X$_1$—C(=O)—, where X$_1$ is a single bond, an oxygen atom, a sulfur atom, an alkylene group, an alkenylene group or an alkynylene group, and W is an aryl group containing at least one halogen atom.

2. The polymer composition according to claim 1, wherein the polymer segment A satisfies at least one of the following conditions 1 to 3:
condition 1: the polymer segment A exhibits a melting transition peak or an isotropic transition peak in a range of −80° C. to 200° C. in a DSC analysis:
condition 2: the polymer segment A exhibits a peak having a half-value width in a range of 0.2 nm$^{-1}$ to 0.9 nm$^{-1}$ within a scattering vector (q) range of 0.5 nm$^{-1}$ to 10 nm$^{-1}$ in an XRD analysis:
condition 3: the polymer segment A comprises a side chain, wherein a number (n) of chain-forming atoms in the side chain satisfies Equation 1 below with the scattering vector (q) in the XRD analysis:

$$3 \text{ nm}^{-1} \leq nq/(2\times\pi) \leq 5 \text{ nm}^{-1}$$ [Equation 1]

wherein, n is the number of the chain-forming atoms and q is the smallest scattering vector (q) in which the peak is observed in the XRD analysis for the block copolymer or the scattering vector (q) in which the peak of the largest peak area is observed.

3. The polymer composition according to claim 1, wherein the polymer segment A in the block copolymer has a volume fraction of 0.3 to 0.7, and a sum of volume fractions of the polymer segment A and the polymer segment B is 1.

4. The polymer composition according to claim 1, wherein the block copolymer has a number average molecular weight in a range of 5,000 to 100,000.

5. The polymer composition according to claim 1, wherein the block copolymer has polydispersity in a range of 1.01 to 1.60.

6. The polymer composition according to claim 1, wherein the random copolymer has a number average molecular weight in a range of 5,000 to 100,000.

7. The polymer composition according to claim 1, wherein the random copolymer has polydispersity in a range of 1.01 to 1.80.

8. A laminate comprising:
a substrate;
a polymer membrane formed on a surface of the substrate, wherein the polymer membrane comprises a block copolymer which comprises a polymer segment A containing a first monomer unit and a polymer segment B having an absolute value of a surface energy difference with the polymer segment A of 10 mN/m or less and the polymer segment B containing a second monomer unit; and
a random copolymer containing the first monomer unit and the second monomer unit, and the second monomer unit in the random copolymer has a volume fraction of 0.3 to 0.7, and a sum of volume fractions of the first monomer unit and the second monomer unit in the random copolymer is 1,
wherein the random copolymer is contained in a ratio of 1 vol % to 50 vol % based on a total volume of the block copolymer and the random copolymer, and
wherein the first monomer unit is a unit represented by formula 1 below:

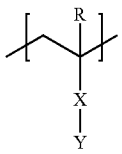

[formula 1]

wherein, R is hydrogen or an alkyl group having 1 to 4 carbon atoms, X is a single bond, an oxygen atom, a sulfur atom, —S(=O)$_2$—, a carbonyl group, an alkylene group, an alkenylene group, —C(=O)—X$_1$— or —X$_1$—C(=O)—, where X$_1$ is an oxygen atom, a sulfur atom, an alkylene group, an alkenylene group or an alkynylene group, and Y is a monovalent substituent comprising a ring structure to which a side chain having 8 or more chain-forming atoms is linked, wherein the second monomer unit is a unit represented by formula 2 below:

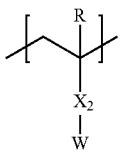

[formula 2]

wherein, R is hydrogen or an alkyl group having 1 to 4 carbon atoms, X$_2$ is a single bond, an oxygen atom, a sulfur atom, —S(=O)$_2$—, an alkylene group, an alkenylene group, —C(=O)—X$_1$— or —X$_1$—C(=O)—, where X$_1$ is a single bond, an oxygen atom, a sulfur atom, an alkylene group, an alkenylene group or an alkynylene group, and W is an aryl group containing at least one halogen atom.

9. The laminate according to claim 8, wherein the block copolymer forms a lamellar structure.

10. The laminate according to claim 9, wherein the polymer membrane has a thickness of 1 L to 10 L, where L is a pitch of the lamellar structure.

11. A method for producing a patterned substrate, comprising:
    coating the polymer composition of claim 1 on a substrate; and
    annealing the polymer composition to form a self-assembled structure of the block copolymer.

12. The method according to claim 11, wherein a neutral layer is not present on the surface of the substrate on which the polymer composition is coated.

13. The method according to claim 12, further comprising:
    selectively removing one of the polymer segments of the block copolymer forming the self-assembled structure.

14. The method according to claim 13, further comprising:
    etching the substrate using the block copolymer from which one of the polymer segments has been removed as a mask.

* * * * *